(12) United States Patent
Schaffer et al.

(10) Patent No.: US 12,052,970 B2
(45) Date of Patent: Aug. 6, 2024

(54) TOMATO PLANT PRODUCING FRUITS WITH MODIFIED SUGAR CONTENT

(71) Applicants: The State of Israel, Ministry of Agriculture & Rural Development, Agricultural Research Organization, Rishon Lezion (IL); Syngenta Participations AG, Basel (CH)

(72) Inventors: Arthur Schaffer, Rishon Lezion (IL); Michal Moy, Richon Lezion (IL); Naomi Houminer, Luzit (IL); Marina Petreikov, Rishon Lezion (IL); Yelena Yeselson, Rishon Lezion (IL); Daniel Rickett, Bracknell (GB); Julien Bonnet, Saint-Sauveur (FR); Charles James Baxter, Research Triangle Park, NC (US)

(73) Assignees: The State of Israel, Ministry of Agriculture & Rural Development, Agricultural Research Organization, Rishon Lezion (IL); Syngenta Participations AG, Basel (CH)

( * ) Notice: Subject to any disclaimer, the term of this patent is extended or adjusted under 35 U.S.C. 154(b) by 138 days.

(21) Appl. No.: 17/285,204

(22) PCT Filed: Oct. 11, 2019

(86) PCT No.: PCT/EP2019/077627
§ 371 (c)(1),
(2) Date: Apr. 14, 2021

(87) PCT Pub. No.: WO2020/078852
PCT Pub. Date: Apr. 23, 2020

(65) Prior Publication Data
US 2021/0321587 A1    Oct. 21, 2021

(30) Foreign Application Priority Data

Oct. 16, 2018 (EP) .................................. 18200806
Nov. 21, 2018 (EP) .................................. 18207600
Jan. 21, 2019 (EP) .................................. 19152831

(51) Int. Cl.
*A01H 5/08* (2018.01)
*A01H 1/00* (2006.01)
*A01H 6/82* (2018.01)
*C12Q 1/6895* (2018.01)

(52) U.S. Cl.
CPC ............. *A01H 6/825* (2018.05); *A01H 1/00* (2013.01); *A01H 1/102* (2021.01); *A01H 5/08* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| 5,658,773 | A  | 8/1997 | Bennett et al. |
| 6,384,300 | B1 | 5/2002 | Rausch et al. |
| 8,093,455 | B2 | 1/2012 | Finkers et al. |

FOREIGN PATENT DOCUMENTS

| AU | 2013200775  |    | 3/2013 |
| JP | 2000188985  | A  | 7/2000 |
| JP | 2000515755  | A  | 11/2000 |
| RU | 2469094     | C2 | 12/2012 |
| WO | 2012095841  | A1 | 7/2012 |

OTHER PUBLICATIONS

Yelle et al., Plant Physiology (1991) 95, 1026-1035.*
Chetelat, R.T. et al: "Introgression into tomato (*Lycopersicon esculentum*) of the L. chmielewskii sucrose accumulator gene (suer) controlling fruit sugar composition". Theoretical and Applied Genetics; International Journal of Plant Breeding Research. Springer. Berlin. DE. vol. 91. No. 2, Jan. 1, 1995 (Jan. 1, 1995). pp. 327-333. XP002443990. ISSN: 0040-5752.
ISR & WrOp for PCT/EP2019/077627, dated Dec. 11, 2019.
EPO; App. No. EP 18200806.0; Extended European Search Report dated Jan. 15, 2019.
Yelle et al., "Sink Metabolism in Tomato Fruit," Plant Physiology (1991) 95, pp. 1026-1035.
Qin, et al., "A Tomato Vacuolar Invertase Inhibitor Mediates Sucrose Metabolism and Influences Fruit Ripening", Plant Physiol, vol. 172(3), pp. 1596-1611, 2016.
Yamamoto, et al., "Expressed sequence tags from the laboratory-grown miniature tomato (Lycopersicon esculentum) cultivar Micro-Tom and mining for single nucleotide polymorphisms and insertions/deletions in tomato cultivars", Gene, 356, pp. 127-134, 2005.

* cited by examiner

*Primary Examiner* — Phuong T Bui
(74) *Attorney, Agent, or Firm* — BakerHostetler; Toni-Junell Herbert

(57) ABSTRACT

The invention relates to novel tomato plants producing fruits displaying a modified sugar content, particularly displaying an increased sucrose content. The invention also relates to seeds and parts of said plants, for example fruits. The invention further relates to methods of making and using such seeds and plants. The invention also relates to a sucrose modifier SucMod allele, which, when combined with a sucrose accumulation TIV allele derived from a green-fruited wild tomato accession, significantly alters the proportion of sugar stored in the fruit, confers increased fruit sucrose content at the expense of hexose sugars and results in a fruit with a distinctive flavor.

19 Claims, 12 Drawing Sheets
Specification includes a Sequence Listing.

CLUSTAL O (1.2.4) multiple sequence alignment

```
S.pennellii_LA0716      ATGAGAAATTTATTCCCCATATTGATGTTAATCACTAATTTATCACTCAACAACGATAAC      60
S.chmil_BD732           ATGAGAAATTTATTCCCCATATTGATGTTAATCACTAATTTGGCACTCAACAACGATAAC      60
S.lycopersicum          ATGAGAAATTTATTCCCCATATTGATGTTACTCACTAATTTGTCACTCAACATCGATAAC      60
S.chees_LA0429          ATGAGAAATTTATTCCCCATATTGATGTTACTCACTAATTTGTCACTCAACATCGATAAC      60
S.pimp_LA1589           ATGAGAAATTTATTCCCCATATTGATGTTACTCACTAATTTGTCACTCAACATCGATAAC      60
                        ****************************** ********* ******** *******

S.pennellii_LA0716      AACAACAACAACAACATCATACGCGCAACGTGTAGGGAGACTCCATACTACTCCCTATGT     120
S.chmil_BD732           AACAACAACAACAACATCATACACGCAACGTGTAGGGAGACTCCATACTACTCCCTATGT     120
S.lycopersicum          AACAACAACAACAACATCATACGCGCAACGTGTAGGGAGACTCCATACTACTCCCTATGT     120
S.chees_LA0429          AACAACAACAACAACATCATACGCGCAACGTGTAGGGAGACTCCATACTACTCCCTATGT     120
S.pimp_LA1589           AACAACAACAACAACATCATACGCGCAACGTGTAGGGAGACTCCATACTACTCCCTATGT     120
                        ********************** *************************************

S.pennellii_LA0716      CTCTCAATCCTAGAATCCGATCCACGTAGCTACGAGGCTGAGGGTAGTGATGATATAACT     180
S.chmil_BD732           CTCTCAGTCCTAGAATCCGATCCACGTAGCTACAAGGCTGAGGGTAGTGATGATATAACC     180
S.lycopersicum          CTCTCAGTCCTAGAATCCGATCCACGTAGCTACAAGGCTGAGGGTAGTGATGATATAACC     180
S.chees_LA0429          CTCTCAGTCCTAGAATCCGATCCACGTAGCTACAAGGCTGAGGGTAGTGATGATATAACC     180
S.pimp_LA1589           CTCTCAGTCCTAGAATCCGATCCACGTAGCTACAAGGCTGAGGGTAGTGATGATATAACC     180
                        ****** ************************** ************************

S.pennellii_LA0716      ACCCTAGGCCTCATCATGGTGGATGCAGTGAAATCAAAGTCTATAGAAATAATGAAAAAG     240
S.chmil_BD732           ACCCTAGGTCTCATCATGGTGGATGCAGTGAAATCAAAGTCTATAGAAATAATGAAAAAG     240
S.lycopersicum          ACCCTAGGCCTCATCATGGTGGATGCGGTGAAATCAAAGTCTATAGAAATAATGAAAAAG     240
S.chees_LA0429          ACCCTAGGCCTCATCATGGTGGATGCGGTGAAATCAAAGTCTATAGAAATAATGAAAAAG     240
S.pimp_LA1589           ACCCTAGGCCTCATCATGGTGGATGCGGTGAAATCAAAGTCTATAGAAATAATGAAAAAG     240
                        ******** ***************** *********************************

S.pennellii_LA0716      CTAAAAGAGCTAGAAAAATCGAACCCTGAGTGGCGGGTCCCACTTAACCAGTGTTACATG     300
S.chmil_BD732           CTAAAAGAGCTAGAGAAATCGAACCCTGAGTGGCGGGTCCCACTTAACCAGTGTTACATG     300
S.lycopersicum          CTAAAAGAGCTAGAGAAATCGAACCCTGAGTGGCGGGTCCCACTTAACCAGTGTTACATG     300
S.chees_LA0429          CTAAAAGAGCTAGAGAAATCGAACCCTGAGTGGCGGGTCCCACTTAACCAGTGTTACATG     300
S.pimp_LA1589           CTAAAAGAGCTAGAGAAATCGAACCCTGAGTGGCGGGTCCCACTTAACCAGTGTTACATG     300
                        ************** *********************************************
                                      310
S.pennellii_LA0716      GTGTATAACACCGTCCTACGAGCCGATGTAACGGTAGCCGTTGAAGCCTTGAAGAGGGGT     360
S.chmil_BD732           GTGTATAACGCCGTCCTACGAGCCGATGTAACGGTAGCCGTTGAAGCCTTGAAGAGGGGT     360
S.lycopersicum          GTGTATAACACCGTCCTACGAGCCGATGTAACGGTAGCCGTTGAAGCCTTGAAGAGGGGT     360
S.chees_LA0429          GTGTATAACACCGTCCTACGAGCCGATGTAACGGTAGCCGTTGAAGCCTTGAAGAGGGGT     360
S.pimp_LA1589           GTGTATAACGCCGTCCTACGAGCCGATGTAACGGTAGCCGTTGAAGCCTTGAAGAGGGGT     360
                        ********* **************************************************

S.pennellii_LA0716      GTCCCTAAATTTGCTGAAGATGGTATGGATGATGTTGTTGTAGAAGCACAAACTTGTGAG     420
S.chmil_BD732           GTCCCTAAATTTGCTGAAGATGGTATGGATGATGTTGTTGTAGAAGCACAAACTTGTGAG     420
S.lycopersicum          GTCCCTAAATTTGCTGAAGATGGTATGGATGATGTTGTTGTAGAAGCACAAACTTGTGAG     420
S.chees_LA0429          GTCCCTAAATTTGCTGAAGATGGTATGGATGATGTTGTTGTAGAAGCACAAACTTGTGAG     420
S.pimp_LA1589           GTCCCTAAATTTGCTGAAGATGGTATGGATGATGTTGTTGTAGAAGCACAAACTTGTGAG     420
                        ************************************************************
```

FIG. 4A

```
S.pennellii_LA0716    TTTAGTTTTAATTATTATAATAAATCGGATTTTCCAATTTCTAATATGAGTAAGGACATA    480
S.chmil_BD732         TTTAGTTTTAATTATTATAATAAATCGGATTTTCCAATTTCTAATATGAGTAAGGACATA    480
S.lycopersicum        TTTAGTTTTAATTATTATAATAAATCGGATTTTCCAATTTCTAATATGAGTAAGGACATA    480
S.chees_LA0429        TTTAGTTTTAATTATTATAATAAATCGGATTTTCCAATTTCTAATATGAGTAAGGACATA    480
S.pimp_LA1589         TTTAGTTTTAATTATTATAATAAATCGGATTTTCCAATTTCTAATATGAGTAAGGACATA    480
                      ************************************************************
                                    498
S.pennellii_LA0716    ATTGAACTCTCAAAAGTCGCTAAATCCATAATTAGAATGTTATTATG    527
S.chmil_BD732         GTTGAACTCTCAAAAGTTGCTAAATCCATAATTAGAATGTTATTATG    527
S.lycopersicum        GTTGAACTCTCAAAAGTCGCTAAATCCATAATTAGAATGTTATTATG    527
S.chees_LA0429        GTTGAACTCTCAAAAGTCGCTAAATCCATAATTAGAATGTTATTATG    527
S.pimp_LA1589         GTTGAACTCTCAAAAGTTGCTAAATCCATAATTAGAATGTTATTATG    527
                      *************** *******************************
```

Identity matrix of VIF sequences

|   | | 1 | 2 | 3 | 4 | 5 |
|---|---|---|---|---|---|---|
| 1: | S.pennelli_LA0716 | 100.00 | 97.91 | 98.29 | 98.29 | 97.91 |
| 2: | S.chmil_BD732 | 97.91 | 100.00 | 98.48 | 98.48 | 98.86 |
| 3: | S.lycopersicum | 98.29 | 98.48 | 100.00 | 100.00 | 99.62 |
| 4: | S.chees_LA0429 | 98.29 | 98.48 | 100.00 | 100.00 | 99.62 |
| 5: | S.pimp_LA1589 | 97.91 | 98.86 | 99.62 | 99.62 | 100.00 |

FIG. 4B

```
                                              41
S.habrochaites      ATGGCCACCCAGTGTTATGACCCCGAAAACTCCGCCTCTCATTACACATTCCTCCCGGAT    60
S.peruvianum        ATGGCCACTCAGTGTTATGACCCCGAAAACTCCGCCTCTCATTACACATTCCTCCCGGAT    60
S.pennellii         ATGGCCACCCAGTGTTATGACCCCGAAAACTCCGCCTCTCACTACACATTCCTCCCGGAT    60
S.chmielewskii      ATGGCCACTCAGTGTTATGACCCCGAAAACTCCGCCTCTCATTACACATTACTCCCGGAT    60
S.lyco cerasiforme  ATGGCCACTCAGTGTTATGACCCCGAAAACTCCGCCTCTCGTTACACATTACTCCCGGAT    60
S.lycopersicum      ATGGCCACTCAGTGTTATGACCCCGAAAACTCCGCCTCTCGTTACACATTACTCCCGGAT    60
S.pimpinellifolium  ATGGCCACTCAGTGTTATGACCCCGAAAACTCCGCCTCTCGTTACACATTACTCCCGGAT    60
S.cheesmaniae       ATGGCCACTCAGTGTTATGACCCCGAAAACTCCGCCTCTCGTTACACATTACTCCCGGAT    60
                    ******* *********************************  ******** ********

S.habrochaites      CAACCCGATTCCGGCCACCGGAAGTCCCTTAAAATCTTCTCCGGCATTTTCCTCTCCGTT   120
S.peruvianum        CAACCCGATTCCGGCCACCGGAAGTCCCTTAAAATCATCTCCGGCATTTTCCTCTCCGTT   120
S.pennellii         CAACCCGATTCCGGCCACCGGAAGTCCCTTAAAATCATCTCCGGCATTTTCCTCTCCGTT   120
S.chmielewskii      CAACCCGATTCCGGCCACCGGAAGTCCCTTAAAATCATCTCCGGCATTTTCCTCTCCGTT   120
S.lyco cerasiforme  CAACCCGATTCCGGCCACCGGAAGTCCCTTAAAATCATCTCCGGCATTTTCCTCTCCGTT   120
S.lycopersicum      CAACCCGATTCCGGCCACCGGAAGTCCCTTAAAATCATCTCCGGCATTTTCCTCTCCGTT   120
S.pimpinellifolium  CAACCCGATTCCGGCCACCGGAAGTCCCTTAAAATCATCTCCGGCATTTTCCTCTCCGTT   120
S.cheesmaniae       CAACCCGATTCCGGCCACCGGAAGTCCCTTAAAATCATCTCCGGCATTTTCCTCTCCGTT   120
                    ************************************ ***********************
                                                                           179
S.habrochaites      TTCCTTTTGCTTTCTGTAGCCTTTTTTCCGATCCTCAACAACCAGTCACCGGACTTGCGA   180
S.peruvianum        TTCCTTTTGCTTTCTGTAGCCTTCTTTCCGATCCTCAACAACCAGTCACCGGACTTGCAA   180
S.pennellii         TTCCTTTTGCTTTCTGTAGCCTTCTTTCCGATCCTCAACAACCAGTCACCGGACTTGCAA   180
S.chmielewskii      TTCCTTTTGCTTTGTGTAGCCTTCTTTCCGATCCTCAACAACCAGTCACCGGACTTGCAA   180
S.lyco cerasiforme  TTCCTTTTGCTTTCTGTAGCCTTCTTTCCGATCCCCAACAACCAGTCACCGGACTTGCAA   180
S.lycopersicum      TTCCTTTTGCTTTCTGTAGCCTTCTTTCCGATCCTCAACAACCAGTCACCGGACTTGCAA   180
S.pimpinellifolium  TTCCTTTTGCTTTCTGTAGCCTTCTTTCCGATCCTCAACAACCAGTCACCGGACTTGCAA   180
S.cheesmaniae       TTCCTTTTGCTTTCTGTAGCCTTCTTTCCGATCCTCAACAACCAGTCACCGGACTTGCAA   180
                    ************* ********* ********** ************************ *

S.habrochaites      ATCGACTCCCGTTCGCCGGCGCCGCCGTCAAGAGGTGTTTCTCAGGGAGTCTCTGATAAA   240
S.peruvianum        ATCGACTCCCGTTCGCCGGCGCCGCCGTCAAGAGGTGTTTCTCAGGGAGTCTCCGATAAA   240
S.pennellii         ATCGACTCCCGTTCGCCGGCGCCGCCGTCAAGAGGTGTTTCTCAGGGAGTCTCCGATAAA   240
S.chmielewskii      ATCGACTCCCGTTCGCCGGCGCCGCCGTCAAGAGGTGTTTCTCAGGGAGTCTCCGATAAA   240
S.lyco cerasiforme  ATCGACTCCCGTTCGCCGGCGCCGCCGTCAAGAGGTGTTTCTCAGGGAGTCTCCGATAAA   240
S.lycopersicum      ATCGACTCCCGTTCGCCGGCGCCGCCGTCAAGAGGTGTTTCTCAGGGAGTCTCCGATAAA   240
S.pimpinellifolium  ATCGACTCCCGTTCGCCGGCGCCGCCGTCAAGAGGTGTTTCTCAGGGAGTCTCCGATAAA   240
S.cheesmaniae       ATCGACTCCCGTTCGCCGGCGCCGCCGTCAAGAGGTGTTTCTCAGGGAGTCTCCGATAAA   240
                    ***************************************************** ******

S.habrochaites      ACTTTTCGAGATGTAGCCGGTGCTAGTCACGTTTCTTATGCGTGGTCCAATGCTATGCTT   300
S.peruvianum        ACTTTTCGAGATGTAGCCGGTGCTAGTCACGTTTCTTATGCGTGGTCCAATGCTATGCTT   300
S.pennellii         ACTTTTCGAGATGTAGCCGGGGCTAGTCACGTTTCTTATGCGTGGTCCAATGCTATGCTT   300
S.chmielewskii      ACTTTTCGAGATGTAGCCGGTGCTAGTCACGTTTCTTATGCGTGGTCCAATGCTATGCTT   300
S.lyco cerasiforme  ACTTTTCGAGATGTAGCCGGTGCTAGTCACGTTTCTTATGCGTGGTCCAATGCTATGCTT   300
S.lycopersicum      ACTTTTCGAGATGTAGCCGGTGCTAGTCACGTTTCTTATGCGTGGTCCAATGCTATGCTT   300
S.pimpinellifolium  ACTTTTCGAGATGTAGCCGGTGCTAGTCACGTTTCTTATGCGTGGTCCAATGCTATGCTT   300
S.cheesmaniae       ACTTTTCGAGATGTAGCCGGTGCTAGTCACGTTTCTTATGCGTGGTCCAATGCTATGCTT   300
                    ******************** ******************* *******************
```

FIG. 5A

```
S.habrochaites        AGCTGGCAAAGAACGGCTTACCATTTTCAACCTCAGAAAAATTGGATGAACGATCCTAAT    360
S.peruvianum          AGCTGGCAAAGAACGGCTTACCATTTTCAACCTCAAAAAATTGGATGAACGATCCTAAT    360
S.pennellii           AGCTGGCAAAGAACTGCTTACCATTTTCAACCTCAAAAAATTGGATGAACGATCCTAAT    360
S.chmielewskii        AGCTGGCAAAGAACGGCTTACCATTTTCAACCTCAAAAAATTGGATGAACGATCCTAAT    360
S.lyco cerasiforme    AGCTGGCAAAGAACGGCTTACCATTTTCAACCTCAAAAAATTGGATGAACGATCCTAAT    360
S.lycopersicum        AGCTGGCAAAGAACGGCTTACCATTTTCAACCTCAAAAAATTGGATGAACGATCCTAAT    360
S.pimpinellifolium    AGCTGGCAAAGAACGGCTTACCATTTTCAACCTCAAAAAATTGGATGAACGATCCTAAT    360
S.cheesmaniae         AGCTGGCAAAGAACGGCTTACCATTTTCAACCTCAAAAAATTGGATGAACGATCCTAAT    360
                      ************** ******************** **********************

S.habrochaites        GGACCATTGTATCACAAGGGATGGTACCACCTTTTTTATCAATACAATCCAGATTCGGCT    420
S.peruvianum          GGACCATTGTATCACAAGGGATGGTACCACCTTTTTTATCAATACAATCCAGATTCAGCT    420
S.pennellii           GGACCATTGTATCACAAGGGATGGTACCACCTTTTTTATCAATACAATCCAGATTCAGCT    420
S.chmielewskii        GGACCATTGTATCACAAGGGATGGTACCACCTTTTTTATCAATACAATCCAGATTCAGCT    420
S.lyco cerasiforme    GGACCATTGTATCACAAGGGATGGTACCACCTTTTTTATCAATACAATCCAGATTCAGCT    420
S.lycopersicum        GGACCATTGTATCACAAGGGATGGTACCACCTTTTTTATCAATACAATCCAGATTCAGCT    420
S.pimpinellifolium    GGACCATTGTATCACAAGGGATGGTACCACCTTTTTTATCAATACAATCCAGATTCAGCT    420
S.cheesmaniae         GGACCATTGTATCACAAGGGATGGTACCACCTTTTTTATCAATACAATCCAGATTCAGCT    420
                      ********************************************************  ***

S.habrochaites        ATTTGGGGAATATCACATGGGGCCATGCTGTATCCAAGGACTTGATCCACTGGCTCTAC    480
S.peruvianum          ATTTGGGGAAATATCACATGGGGCCATGCTGTATCCAAGGACTTGATCCACTGGCTCTAC   480
S.pennellii           ATTTGGGGAAATATCACATGGGGCCATGCTGTATCCAAGGACTTGATCCACTGGCTCTAC   480
S.chmielewskii        ATTTGGGGAAATATCACATGGGGCCATGCTGTATCCAAGGACTTGATCCACTGGCTCTAC   480
S.lyco cerasiforme    ATTTGGGGAAATATCACATGGGGCCATGCTGTATCCAAGGACTTGATCCACTGGCTCTAC   480
S.lycopersicum        ATTTGGGGAAATATCACATGGGGCCATGCTGTATCCAAGGACTTGATCCACTGGCTCTAC   480
S.pimpinellifolium    ATTTGGGGAAATATCACATGGGGCCATGCTGTATCCAAGGACTTGATCCACTGGCTCTAC   480
S.cheesmaniae         ATTTGGGGAAATATCACATGGGGCCATGCTGTATCCAAGGACTTGATCCACTGGCTCTAC   480
                      ******* ****************************************************

S.habrochaites        TTGCCTTTTGCCATGGTTCCTGATCAGTGGTATGATATTAACGGTGTCTGGACAGGGTCC   540
S.peruvianum          TTGCCTTTTGCCATGGTTCCTGATCAATGGTATGATATTAACGGTGTCTGGACAGGGTCC   540
S.pennellii           TTGCCTTTTGCCATGGTTCCTGATCAATGGTATGATATTAACGGTGTCTGGACTGGGTCC   540
S.chmielewskii        TTGCCTTTTGTCATGGTTCCTGATCAATGGTATGATATTAATGGTGTCTGGACTGGGTCC   540
S.lyco cerasiforme    TTGCCTTTTGCCATGGTTCCTGATCAATGGTATGATATTAACGGTGTCTGGACAGGGTCC   540
S.lycopersicum        TTGCCTTTTGCCATGGTTCCTGATCAATGGTATGATATTAACGGTGTCTGGACAGGGTCC   540
S.pimpinellifolium    TTGCCTTTTGCCATGGTTCCTGATCAATGGTATGATATTAACGGTGTCTGGACAGGGTCC   540
S.cheesmaniae         TTGCCTTTTGCCATGGTTCCTGATCAATGGTATGATATTAACGGTGTCTGGACAGGGTCC   540
                      ********* ************** ************** ********** ******

S.habrochaites        GCTACCATCCTACCCGATGGTCAGATCATGATGCTTTATACCGGTGACACGGATGATTAT   600
S.peruvianum          GCTACCATCCTACCCGATGGTCAGATCATGATGCTTTATACCGGTGACACTGATGATTAT   600
S.pennellii           GCTACCATCCTACCCGATGGTCAGATCATGATGCTTTATACCGGTGACACTGATGATTAT   600
S.chmielewskii        GCTACCATCCTACCCGATGGTCAGATCATGATGCTTTATACCGGTGACACTGATGATTAT   600
S.lyco cerasiforme    GCTACCATCCTACCCGATGGTCAGATCATGATGCTTTATACCGGTGACACTGATGATTAT   600
S.lycopersicum        GCTACCATCCTACCCGATGGTCAGATCATGATGCTTTATACCGGTGACACTGATGATTAT   600
S.pimpinellifolium    GCTACCATCCTACCCGATGGTCAGATCATGATGCTTTATACCGGTGACACTGATGATTAT   600
S.cheesmaniae         GCTACCATCCTACCCGATGGTCAGATCATGATGCTTTATACCGGTGACACTGATGATTAT   600
                      ********************************************** ********

S.habrochaites        GTACAAGTGCAAAATCTTGCGTACCCCGCCAACTTATCTGATCCTCTCCTTCTAGACTGG   660
S.peruvianum          GTGCAAGTGCAAAATCTTGCGTACCCCGCCAACTTATCTGATCCTCTCCTTCTAGACTGG   660
S.pennellii           GTGCAAGTGCAAAATCTTGCGTAGCCCGCCAACTTATCTGATCCTCTCCTTCTAGACTGG   660
S.chmielewskii        GTGCAAGTGCAAAATCTTGCGTACCCCGCCAACTTATCTGATCCTCTCCTTCTAGACTGG   660
S.lyco cerasiforme    GTGCAAGTGCAAAATCTTGCGTACCCCGCCAACTTATCTGATCCTCTCCTTCTAGACTGG   660
S.lycopersicum        GTGCAAGTGCAAAATCTTGCGTACCCCGCCAACTTATCTGATCCTCTCCTTCTAGACTGG   660
S.pimpinellifolium    GTGCAAGTGCAAAATCTTGCGTACCCCGCCAACTTATCTGATCCTCTCCTTCTAGACTGG   660
S.cheesmaniae         GTGCAAGTGCAAAATCTTGCGTACCCCGCCAACTTATCTGATCCTCTCCTTCTAGACTGG   660
                      ** ******************** ************************************
                                                                             668
S.habrochaites        GTCAAGTACAAAGGCAACCCGGTTCTGGTTCCTCCACCCGGCATTGGGGTCAAGGACTTT   720
S.peruvianum          GTCAAGTACAAAGGCAACCCGGTTCTGGTTCCTCCACCCGGCATTGGGGTCAAGGACTTT   720
S.pennellii           GTCAAGTACAAAGGCAACCCGGTTCTGGTTCCTCCACCCGGCATTGCTGTCAAGGACTTT   720
S.chmielewskii        GTCAAGTACAAAGGCAACCCGGTTCTGGTTCCTCCACCCGGCATTGGGGTCAAGGACTTT   720
S.lyco cerasiforme    GTCAAGTTCAAAGGCAACCCGGTTCTGGTTCCTCCACCCGGCATTGGTGTCAAGGACTTT   720
S.lycopersicum        GTCAAGTTCAAAGGCAACCCGGTTCTGGTTCCTCCACCCGGCATTGGTGTCAAGGACTTT   720
S.pimpinellifolium    GTCAAGTTCAAAGGCAACCCGGTTCTGGTTCCTCCACCCGGCATTGGTGTCAAGGACTTT   720
S.cheesmaniae         GTCAAGTTCAAAGGCAACCCGGTTCTGGTTCCTCCACCCGGCATTGGTGTCAAGGACTTT   720
                      ******* ************************************    ***********
```

FIG. 5B

```
S.habrochaites       AGAGACCCGACTACTGCTTGGACCGGACCGCAAAATGGGCAATGGCTGTTAACAATCGGG    780
S.peruvianum         AGGGACCCGACTACTGCTTGGACCGGACCGCAAAATGGGCAATGGCTGTTAACAATCGG     780
S.pennellii          AGAGACCCGACTACTGCTTGGACCGGACCGCAAAATGGGCAATGGCTGTTAACAATCGGG    780
S.chmielewskii       AGAGACCCGACTACTGCTTGGACCGGACCGCAAAATGGGCAATGGCTGTTAACAATCGGG    780
S.lyco cerasiforme   AGAGACCCGACTACTGCTTGGACCGGACCACAAAATGGGCAATGGCTGTTAACAATCGGG    780
S.lycopersicum       AGAGACCCGACTACTGCTTGGACCGGACCACAAAATGGGCAATGGCTGTTAACAATCGGG    780
S.pimpinellifolium   AGAGACCCGACTACTGCTTGGACCGGACCACAAAATGGGCAATGGCTGTTAACAATCGGG    780
S.cheesmaniae        AGAGACCCGACTACTGCTTGGACCGGACCACAAAATGGGCAATGGCTGTTAACAATCGGG    780
                     ** **************************  ******************************

S.habrochaites       TCCAAGATTGGTAAAACGGGTATTGCACTTGTTTATGAAACTTCCAACTTCACAAGCTTT    840
S.peruvianum         TCTAAGATTGGTAAAGCGGGTATTGCACTTGTTTATGAAACTTCCAACTTCACAAGCTTT    840
S.pennellii          TCTAAGATTGGTAAAACGGGTATTGCACTTGTTTATGAAACTTCCAACTTCACAAGCTTT    840
S.chmielewskii       TCTAAGATTGGTAAAACGGGTGTTGCACTTGTTTATGAAACTTCCAACTTCACAAGCTTT    840
S.lyco cerasiforme   TCTAAGATTGGTAAAACGGGTGTTGCACTTGTTTATGAAACTTCCAACTTCACAAGCTTT    840
S.lycopersicum       TCTAAGATTGGTAAAACGGGTGTTGCACTTGTTTATGAAACTTCCAACTTCACAAGCTTT    840
S.pimpinellifolium   TCTAAGATTGGTAAAACGGGTGTTGCACTTGTTTATGAAACTTCCAACTTCACAAGCTTT    840
S.cheesmaniae        TCTAAGATTGGTAAAACGGGTGTTGCACTTGTTTATGAAACTTCCAACTTCACAAGCTTT    840
                     ** ************ ***** **************************************

S.habrochaites       AAGCTATTGGATGGAGTGCTGCATGCGGTTCCGGGTACGGGTATGTGGGAGTGTGTGGAC    900
S.peruvianum         AAGCTATTGGATGGAGTGCTGCATGCGGTTCCGGGTACGGGTATGTGGGAGTGTGTGGAC    900
S.pennellii          AAGCTATTGGATGGAGTGCTGCATGCGGTTCCGGGTACGGGTATGTGGGAGTGTGTGGAC    900
S.chmielewskii       AAGCTATTGGATGGAGTGCTGCATGCGGTTCCGGGTACGGGTATGTGGGAGTGCGTGGAC    900
S.lyco cerasiforme   AAGCTATTGGATGGAGTGCTGCATGCGGTTCCGGGTACGGGTATGTGGGAGTGTGTGGAC    900
S.lycopersicum       AAGCTATTGGATGGAGTGCTGCATGCGGTTCCGGGTACGGGTATGTGGGAGTGTGTGGAC    900
S.pimpinellifolium   AAGCTATTGGATGGAGTGCTGCATGCGGTTCCGGGTACGGGTATGTGGGAGTGTGTGGAC    900
S.cheesmaniae        AAGCTATTGGATGGAGTGCTGCATGCGGTTCCGGGTACGGGTATGTGGGAGTGTGTGGAC    900
                     ***************************************************** ******

930
S.habrochaites       TTTTACCCGGTGTCTACTAAAAAAACAAATGGGTTGGACACATCATATAACGGGCCGGGT    960
S.peruvianum         TTTTACCCGGTATCTACTAAAAAAACAAATGGGTTGGACACATCATATAACGGGCCGGGT    960
S.pennellii          TTTTACCCGGTATCTACTAAAAAAACAAATGGGTTGGACACATCATATAACGGGCCGGGT    960
S.chmielewskii       TTTTACCCGGTATCTACTAAAAAAACAAATGGGTTGGACACATCATATAACGGGCCGGGT    960
S.lyco cerasiforme   TTTTACCCGGTATCTACTAAAAAAACAAACGGGTTGGACACATCATATAACGGGCCGGGT    960
S.lycopersicum       TTTTACCCGGTATCTACTAAAAAAACAAACGGGTTGGACACATCATATAACGGGCCGGGT    960
S.pimpinellifolium   TTTTACCCGGTATCTACTAAAAAAACAAACGGGTTGGACACATCATATAACGGGCCGGGT    960
S.cheesmaniae        TTTTACCCGGTATCTACTAAAAAAACAAACGGGTTGGACACATCATATAACGGGCCGGGT    960
                     ********** ****************** ******************************

S.habrochaites       GTAAAGCATGTGTTAAAAGCAAGTTTAGATGACAATAAGCAAGATCATTATGCTATTGGT   1020
S.peruvianum         GTAAAGCATGTGTTAAAAGCAAGTTTAGATGGCAATAAGCAAGATCATTATGCTATTGGT   1020
S.pennellii          GTAAAGCATGTTTTAAAAGCAAGTTTAGATGACAATAAGCAAGATCATTATGCTATTGGT   1020
S.chmielewskii       GTAAAGCATGTGTTAAAAGCAAGTTTAGATGACAATAAGCAAGATCATTATGCTATTGGG   1020
S.lyco cerasiforme   GTAAAGCATGTGTTAAAAGCAAGTTTAGATGACAATAAGCAAGATCATTATGCTATTGGT   1020
S.lycopersicum       GTAAAGCATGTGTTAAAAGCAAGTTTAGATGACAATAAGCAAGATCATTATGCTATTGGT   1020
S.pimpinellifolium   GTAAAGCATGTGTTAAAAGCAAGTTTAGATGACAATAAGCAAGATCATTATGCTATTGGT   1020
S.cheesmaniae        GTAAAGCATGTGTTAAAAGCAAGTTTAGATGACAATAAGCAAGATCATTATGCTATTGGT   1020
                     *********** ****************** *****************************

1034              1056
S.habrochaites       ACGTATGACTTGACAAAGAACAAATGGACACCCGACAACCCGGAATTKGATTGTGGAATT   1080
S.peruvianum         ACGTATGACTTGCAAAGAACAAATGGACACCCGATAACCCGGAATTGGATTGTGGAATT    1080
S.pennellii          ACGTATGACTTGACAAAGAACAAATGGACGCCCGATAACCCGGAATTGGATTGTGGAATT   1080
S.chmielewskii       ACGTATGACTTGGCAAAGAACAAATGGACACCCGATAACCCGGAATTGGATTGTGGAATT   1080
S.lyco cerasiforme   ACGTATGACTTGGGAAAGAACAAATGGACACCCGATAACCCGGAATTGGATTGTGGAATT   1080
S.lycopersicum       ACGTATGACTTGGGAAAGAACAAATGGACACCCGATAACCCGGAATTGGATTGTGGAATT   1080
S.pimpinellifolium   ACGTATGACTTGGGAAAGAACAAATGGACACCCGATAACCCGGAATTGGATTGTGGAATT   1080
S.cheesmaniae        ACGTATGACTTGGGAAAGAACAAATGGACACCCGATAACCCGGAATTGGATTGTGGAATT   1080
                     **********  ***************** **** ***** ******* ************

S.habrochaites       GGGTTGAGACTAGACTATGGGAAATATTATGCATCAAAGACTTTTTATGACCCGAAGAAA   1140
S.peruvianum         GGGTTGAGACTAGACTATGGGAAATATTATGCATCAAAGACTTTTTATGACCCGAAGAAA   1140
S.pennellii          GGGTTGAGACTAGACTATGGGAAATATTATGCATCAAAGACTTTTTATGACCCGAAGAAA   1140
S.chmielewskii       GGGTTGAGACTAGACTATGGGAAATATTATGCACCAAAGACTTTTTATGACCCGAAGAAA   1140
S.lyco cerasiforme   GGGTTGAGACTAGACTATGGGAAATATTATGCATCAAAGACTTTTTATGACCCGAAGAAA   1140
S.lycopersicum       GGGTTGAGACTAGACTATGGGAAATATTATGCATCAAAGACTTTTTATGACCCGAAGAAA   1140
S.pimpinellifolium   GGGTTGAGACTAGACTATGGGAAATATTATGCATCAAAGACTTTTTATGACCCGAAGAAA   1140
S.cheesmaniae        GGGTTGAGACTAGACTATGGGAAATATTATGCATCAAAGACTTTTTATGACCCGAAGAAA   1140
                     ************ ******************** **************************
```

FIG. 5C

```
S.habrochaites      CAACGAAGAGTACTGTGGGGATGGATTGGGGAAACTGACAGTGAATCTGCTGACCTGCAG    1200
S.peruvianum        GAACGAAGAGTACTGTGGGGATGGATTGGGGAAACTGACAGTGAATCTGCTGACCTGCAG    1200
S.pennellii         CAACGAAGAGTACTGTGGGGATGGATTGGGGAAACTGACAGTGAATCTGCTGACCTGCAG    1200
S.chmielewskii      GAACGAAGAGTACTGTGGGGATGGATTGGGGAAACTGACAGTGAATCTGCTGACCTGCAG    1200
S.lyco cerasiforme  GAACGAAGAGTACTGTGGGGATGGATTGGGGAAACTGACAGTGAATCTGCTGACCTGCAG    1200
S.lycopersicum      GAACGAAGAGTACTGTGGGGATGGATTGGGGAAACTGACAGTGAATCTGCTGACCTGCAG    1200
S.pimpinellifolium  GAACGAAGAGTACTGTGGGGATGGATTGGGGAAACTGACAGTGAATCTGCTGACCTGCAG    1200
S.cheesmaniae       GAACGAAGAGTACTGTGGGGATGGATTGGGGAAACTGACAGTGAATCTGCTGACCTGCAG    1200
                    ************************************************************

S.habrochaites      AAGGGATGGGCATCTGTACAGAGTATTCCAAGGACAGTGCTTTACGACAAGAAGACAGGG    1260
S.peruvianum        AAGGGATGGGCATCTGTACAGAGTATTCCAAGGACAGTGCTTTACGACAATAAGACAGGG    1260
S.pennellii         AAGGGATGGGCATCTGTACAGAGTATTCCAAGGACAGTGCTTTACGACAAGAAGACAGGG    1260
S.chmielewskii      AAGGGATGGGCATCTGTAA---GTATTCCAAGGACAGTGCTTTACGACAAGAAGACAGGG    1257
S.lyco cerasiforme  AAGGGATGGGCATCTGTACAGAGTATTCCAAGGACAGTGCTTTACGACAAGAAGACAGGG    1260
S.lycopersicum      AAGGGATGGGCATCTGTACAGAGTATTCCAAGGACAGTGCTTTACGACAAGAAGACAGGG    1260
S.pimpinellifolium  AAGGGATGGGCATCTGTACAGAGTATTCCAAGGACAGTGCTTTACGACAAGAAGACAGGG    1260
S.cheesmaniae       AAGGGATGGGCATCTGTACAGAGTATTCCAAGGACAGTGCTTTACGACAAGAAGACAGGG    1260
                    ******************    *************************** *********
                                                                         1319
S.habrochaites      ACACATCTACTTCAGTGGCCAGTGGAAGAAATTGAAAGCTTAAGAGTGGGTGATCCTATT    1320
S.peruvianum        ACACATCTACTTCAGTGGCCAGTGGAAGAAATTGAAAGCTTAAGAGTGGGTGATCCTATT    1320
S.pennellii         ACACATCTACTTCAGTGGCCAGTGGAAGAAATTGAAAGCTTAAGAGTGGGTGATCCTATT    1320
S.chmielewskii      ACACATCTACTTCAGTGGCCAGTGGAAGAAATTGAAAGCTTAAGAGTGGGTGATCCTATT    1317
S.lyco cerasiforme  ACACATCTACTTCAGTGGCCAGTGGAAGAAATTGAAAGCTTAAGAGTGGGTGATCCTACT    1320
S.lycopersicum      ACACATCTACTTCAGTGGCCAGTGGAAGAAATTGAAAGCTTAAGAGTGGGTGATCCTACT    1320
S.pimpinellifolium  ACACATCTACTTCAGTGGCCAGTGGAAGAAATTGAAAGCTTAAGAGTGGGTGATCCTACT    1320
S.cheesmaniae       ACACATCTACTTCAGTGGCCAGTGGAAGAAATTGAAAGCTTAAGAGTGGGTGATCCTACT    1320
                    *********************************************************** *

S.habrochaites      GTTAAGCAAGTCGATCTTCAACCAGGCTCAATTGAGCTACTCCGTGTTGACTCAGCTGCA    1380
S.peruvianum        GTTAAGGAAGTCGATCTTCAACCAGGCTCAATTGAGCTACTCCGTGTTGACTCAGCTGCA    1380
S.pennellii         GTTAAGCAAGTCGATCTTCAACCAGGCTCAATTGAGCTACTCCGTGTTGACTCAGCTGCA    1380
S.chmielewskii      GTTAAGCAAGTCGATCTTCAACCAGGCTCAATTGAGCTACTCCGTGTTGACTCAGCTGCA    1377
S.lyco cerasiforme  GTTAAGCAAGTCGATCTTCAACCAGGCTCAATTGAGCTACTCCGTGTTGACTCAGCTGCA    1380
S.lycopersicum      GTTAAGCAAGTCGATCTTCAACCAGGCTCAATTGAGCTACTCCGTGTTGACTCAGCTGCA    1380
S.pimpinellifolium  GTTAAGCAAGTCGATCTTCAACCAGGCTCAATTGAGCTACTCCGTGTTGACTCAGCTGCA    1380
S.cheesmaniae       GTTAAGCAAGTCGATCTTCAACCAGGCTCAATTGAGCTACTCCGTGTTGACTCAGCTGCA    1380
                    ****** *****************************************************

S.habrochaites      GAGTTGGATATAGAAGTCTCATTTGAAGTGGACAAAGTCGCGCTTCAGGGAATAATTGAA    1440
S.peruvianum        GAGTTGGATATAGAAGTCTCATTTGAAGTGGACAAAGTCGCGCTTCAGGGAATAATTGAA    1440
S.pennellii         GAGTTGGATATAGAAGTCTCATTTGAAGTGGACAAAGTCGCGCTTCAGGGAATAATTGAA    1440
S.chmielewskii      GAGTTGGATATAGAAGTCTCATTTGAAGTGGACAAAGTCGCGCTTCAGGGAATAATTGAA    1437
S.lyco cerasiforme  GAGTTGGATATAGAAGTCTCATTTGAAGTGGACAAAGTCGCGCTTCAGGGAATAATTGAA    1440
S.lycopersicum      GAGTTGGATATAGAAGCCTCATTTGAAGTGGACAAAGTCGCGCTTCAGGGAATAATTGAA    1440
S.pimpinellifolium  GAGTTGGATATAGAAGCCTCATTTGAAGTGGACAAAGTCGCGCTTCAGGGAATAATTGAA    1440
S.cheesmaniae       GAGTTGGATATAGAAGCCTCATTTGAAGTGGACAAAGTCGCGCTTCAGGGAATAATTGAA    1440
                    **************** *******************************************

S.habrochaites      GCAGATCATGTTGGTTTCAGTTGCTCTACTAGTGGAGGTGCTGCTAGCAGAGGCATTTTG    1500
S.peruvianum        GAAGATCATGTAGGTTTCAGTTGCTCTACTAGTGGAGGTGCTGCTAGCAGAGGCATTTTG    1500
S.pennellii         GCAGATCATGTAGGTTTCAGTTGCTCTACTAGTGGAGGTGCTGCTAGCAGAGGCATTTTG    1500
S.chmielewskii      GCAGATCATGTAGGTTTCAGTTGCTCTACTAGTGGAGGTGCTGCTAGCAGAGGCATTTTG    1497
S.lyco cerasiforme  GCAGATCATGTAGGTTTCAGTTGCTCTACTAGTGGAGGTGCTGCTAGCAGAGGCATTTTG    1500
S.lycopersicum      GCAGATCATGTAGGTTTCAGTTGCTCTACTAGTGGAGGTGCTGCTAGCAGAGGCATTTTG    1500
S.pimpinellifolium  GCAGATCATGTAGGTTTCAGTTGCTCTACTAGTGGAGGTGCTGCTAGCAGAGGCATTTTG    1500
S.cheesmaniae       GCAGATCATGTAGGTTTCAGTTGCTCTACTAGTGGAGGTGCTGCTAGCAGAGGCATTTTG    1500
                    * ******** *************************************************

S.habrochaites      GGACCGTTTGGTGTCATAGTGATTGCTGATCAAACGCTATCTGAGCTAACGCCAGTTTAC    1560
S.peruvianum        GGACCATTTGGTGTCATAGTAATTGCTGATCAAACGCTATCTGAATTAACGCCAGTTTAC    1560
S.pennellii         GGACCATTTGGTGTCATAGTAATTGCTGATCAAACGCTATCTGAGCTAACGCCAGTTTAC    1560
S.chmielewskii      GGACCATTTGGTGTCATAGTAATTGCTGATCAAACGCTATCTGAGCTAACGCCAGTTTAC    1557
S.lyco cerasiforme  GGACCATTTGGTGTCATAGTAATTGCTGATCAAACGCTATCTGAGCTAACGCCAGTTTAC    1560
S.lycopersicum      GGACCATTTGGTGTCATAGTAATTGCTGATCAAACGCTATCTGAGCTAACGCCAGTTTAC    1560
S.pimpinellifolium  GGACCATTTGGTGTCATAGTAATTGCTGATCAAACGCTATCTGAGCTAACGCCAGTTTAC    1560
S.cheesmaniae       GGACCATTTGGTGTCATAGTAATTGCTGATCAAACGCTATCTGAGCTAACGCCAGTTTAC    1560
                    ***** ************** ********************** *** ************
```

FIG. 5D

```
                     1563
S.habrochaites       TTCTACATTTCTAAAGGAGCTGATGGTCGTGCAGAGACTCACTTCTGTGCTGATCAAACT    1620
S.peruvianum         TTCTACATTTCTAAAGGAGCTGATGGTCGTGCAGAGACTCACTTCTGTGCTGATCAAACT    1620
S.pennellii          TTCTACATTTCTAAAGGAGCTGATGGTCGTGCAGAGACTCACTTCTGTGCTGATCAAACT    1620
S.chmielewskii       TTCTACATTTCTAAAGGAGCTGATGGTCGTGCAGAGACTCACTTCTGTGCTGATCAAACT    1617
S.lyco cerasiforme   TTTTACATTTCTAAAGGAGCTGATGGTCGTGCAGAGACTCACTTCTGTGCTGATCAAACT    1620
S.lycopersicum       TTTTACATTTCTAAAGGAGCTGATGGTCGTGCAGAGACTCACTTCTGTGCTGATCAAACT    1620
S.pimpinellifolium   TTTTACATTTCTAAAGGAGCTGATGGTCGTGCAGAGACTCACTTCTGTGCTGATCAAACT    1620
S.cheesmaniae        TTTTACATTTCTAAAGGAGCTGATGGTCGTGCAGAGACTCACTTCTGTGCTGATCAAACT    1620
                     ** *********************************************************
                          1629
S.habrochaites       AGATCCTCAGAGGCTCCGGGAGTTGGTAAACAAGTTTATGGTAGTTCAGTACCTGTGTTG    1680
S.peruvianum         AGATCCTCAGAGGCTCCGGGAGTTGGTAAACAAGTTTATGGTAGTTCAGTACCTGTGTTG    1680
S.pennellii          AGATCCTCAGAGGCTCCGGGAGTTGGTAAACAAGTTTATGGTAGTTCAGTACCTGTGTTG    1680
S.chmielewskii       AGATCCTCAGAGGCTCCGGAGTTGGTAAACAAGTTTATGGTAGTTCAGTACCTGTGTTG    1677
S.lyco cerasiforme   AGATCCTCTGAGGCTCCGGGAGTTGGTAAACAAGTTTATGGTAGTTCAGTACCTGTGTTG    1680
S.lycopersicum       AGATCCTCTGAGGCTCCGGGAGTTGGTAAACAAGTTTATGGTAGTTCAGTACCTGTGTTG    1680
S.pimpinellifolium   AGATCCTCTGAGGCTCCGGGAGTTGGTAAACAAGTTTATGGTAGTTCAGTACCTGTGTTG    1680
S.cheesmaniae        AGATCCTCTGAGGCTCCGGGAGTTGGTAAACAAGTTTATGGTAGTTCAGTACCTGTGTTG    1680
                     ********  **************************************************

S.habrochaites       GACGGTGAAAAACATTCAATGAGATTATTGGTGGATCACTCAATTGTGGAGAGCTTTGCT    1740
S.peruvianum         GACGGTGAAAAACACTCAATGAGATTATTGGTGGATCACTCAATTGTGGAGAGCTTTGCT    1740
S.pennellii          GACGGTGAAAAACACTCAATGAGATTATTGGTGGATCACTCAATTGTGGAGAGCTTTGCT    1740
S.chmielewskii       GACGGTGAAAAACATTCAATGAGATTATTGGTGGATCACTCAATTGTGGAGAGCTTTGCT    1737
S.lyco cerasiforme   GACGGTGAAAAACATTCAATGAGATTATTGGTGGATCACTCAATTGTGGAGAGCTTTGCT    1740
S.lycopersicum       GACGGTGAAAAACATTCAATGAGATTATTGGTGGATCACTCAATTGTGGAGAGCTTTGCT    1740
S.pimpinellifolium   GACGGTGAAAAACATTCAATGAGATTATTGGTGGATCACTCAATTGTGGAGAGCTTTGCT    1740
S.cheesmaniae        GACGGTGAAAAACATTCAATGAGATTATTGGTGGATCACTCAATTGTGGAGAGCTTTGCT    1740
                     ************** *********************************************

S.habrochaites       CAAGGAGGAAGAACAGTCATAGCATCGCGAATTTACCCAACAAAGGCAGCAAATGGAGCA    1800
S.peruvianum         CAAGGAGGAAGAACAGTCATAACATCGCGAATTTACCCAACAAAGGCAGTAGATGGAGCA    1800
S.pennellii          CAAGGAGGAAGAACAGTCATAACATCGCGAATTTACCCAACAAAGGCAGTAAATGGAGCA    1800
S.chmielewskii       CAAGGAGGAAGAACAGTCATAACATCGCGAATTTACCCAACAAAGGCAGTAAATGGAGCA    1797
S.lyco cerasiforme   CAAGGAGGAAGAACAGTCATAACATCGCGAATTTACCCAACAAAGGCAGTAAATGGAGCA    1800
S.lycopersicum       CAAGGAGGAAGAACAGTCATAACATCGCGAATTTACCCAACAAAGGCAGTAAATGGAGCA    1800
S.pimpinellifolium   CAAGGAGGAAGAACAGTCATAACATCGCGAATTTACCCAACAAAGGCAGTAAATGGAGCA    1800
S.cheesmaniae        CAAGGAGGAAGAACAGTCATAACATCGCGAATTTACCCAACAAAGGCAGTAAATGGAGCA    1800
                     ********************* ************************** * ********

S.habrochaites       GCACGACTCTTCGTTTTCAACAATGCTACAGGGGCTAGCGTTACTGCCTCCGTCAAGATT    1860
S.peruvianum         GCACGACTCTTCGTTTTCAACAATGCCACAGGGGCTAGCGTTACTGCCTCCGTCAAGATT    1860
S.pennellii          GCACGACTCTTCGTTTTCAACAATGCCACAGGGGCTAGCGTTACTGCCTCCGTCAAGATT    1860
S.chmielewskii       GCACGACTCTTTGTTTTCAACAATGCCACAGGGGCTAGCGTTACTGCCTCCGTCAAGATT    1857
S.lyco cerasiforme   GCACGACTCTTTGTTTTCAACAATGCCACAGGGGCTAGCGTTACTGCCTCCGTCAAGATT    1860
S.lycopersicum       GCACGACTCTTTGTTTTCAACAATGCCACAGGGGCTAGCGTTACTGCCTCCGTCAAGATT    1860
S.pimpinellifolium   GCACGACTCTTTGTTTTCAACAATGCCACAGGGGCTAGCGTTACTGCCTCCGTCAAGATT    1860
S.cheesmaniae        GCACGACTCTTTGTTTTCAACAATGCCACAGGGGCTAGCGTTACTGCCTCCGTCAAGATT    1860
                     *********** ************* **********************************
                                                        1886
S.habrochaites       TGGTCACTTGACTCAGCTAATATTCGATCCCTCCCTTTGCAAGACTTGTAA    1911
S.peruvianum         TGGTCAATTGAGTCAGCTAATATTCGATCCTTCCCTTTGCAAGACTTGTAA    1911
S.pennellii          TGGTCACTTGAGTCAGCTAATATTCGATCCTTCCCTTTGCAAGACTTGTAA    1911
S.chmielewskii       TGGCCACTTGAGTCAGCTAATATTCGATCCTTCCCTTTGCAAGACTTGTAA    1908
S.lyco cerasiforme   TGGTCACTTGAGTCAGCTAATATTCAATCCTTCCCTTTGCAAGACTTGTAA    1911
S.lycopersicum       TGGTCACTTGAGTCAGCTAATATTCAATCCTTCCCTTTGCAAGACTTGTAA    1911
S.pimpinellifolium   TGGTCACTTGAGTCAGCTAATATTCAATCCTTCCCTTTGCAAGACTTGTAA    1911
S.cheesmaniae        TGGTCACTTGAGTCAGCTAATATTCAATCCTTCCCTTTGCAAGACTTGTAA    1911
                     *** ** **** *************  **** *******************
```

FIG. 5E

| | | | | | | | | |
|---|---|---|---|---|---|---|---|---|
| S.habrochaites | 100.00 | 98.06 | 98.38 | 98.06 | 97.96 | 97.96 | 97.96 | 97.91 |
| S.peruvianum | 98.06 | 100.00 | 98.95 | 98.74 | 98.74 | 98.74 | 98.74 | 98.69 |
| S.pennellii | 98.38 | 98.95 | 100.00 | 98.85 | 98.74 | 98.74 | 98.74 | 98.69 |
| S.chmielewskii | 98.06 | 98.74 | 98.85 | 100.00 | 98.95 | 98.95 | 98.95 | 98.90 |
| S.lycopersicum | 97.96 | 98.74 | 98.74 | 98.95 | 100.00 | 100.00 | 100.00 | 99.95 |
| S.pimpinellifolium | 97.96 | 98.74 | 98.74 | 98.95 | 100.00 | 100.00 | 100.00 | 99.95 |
| S.cheesmaniae | 97.96 | 98.74 | 98.74 | 98.95 | 100.00 | 100.00 | 100.00 | 99.95 |
| S.lycop cerasiforme | 97.91 | 98.69 | 98.69 | 98.90 | 99.95 | 99.95 | 99.95 | 100.00 |

FIG. 5F

SEQUENCE LISTING

```
<160> NUMBER OF SEQ ID NOS: 25

<210> SEQ ID NO 1
<211> LENGTH: 527
<212> TYPE: DNA
<213> ORGANISM: Solanum chmielewskii

<400> SEQUENCE: 1
atgagaaatt tattccccat attgatgtta atcactaatt tggcactcaa caacgataac      60
aacaacaaca acaacatcat acacgcaacg tgtagggaga ctccatacta ctccctatgt     120
ctctcagtcc tagaatccga tccacgtagc tacaaggctg agggtagtga tgatataacc     180
accctaggtc tcatcatggt ggatgcagtg aaatcaaagt ctatagaaat aatgaaaaag     240
ctaaaagagc tagagaaatc gaaccctgag tggcgggtcc cacttaacca gtgttacatg     300
gtgtataacg ccgtcctacg agccgatgta acggtagccg ttgaagcctt gaagaggggt     360
gtccctaaat ttgctgaaga tggtatggat gatgttgttg tagaagcaca aacttgtgag     420
tttagtttta attattataa taaatcggat tttccaattt ctaatatgag taaggacata     480
gttgaactct caaaagttgc taaatccata attagaatgt tattatg                   527

<210> SEQ ID NO 2
<211> LENGTH: 16
<212> TYPE: DNA
<213> ORGANISM: Artificial Sequence
<220> FEATURE:
<223> OTHER INFORMATION: Forward Primer

<400> SEQUENCE: 2
gggtcccact taacca                                                      16

<210> SEQ ID NO 3
<211> LENGTH: 16
<212> TYPE: DNA
<213> ORGANISM: Artificial Sequence
<220> FEATURE:
```

<223> OTHER INFORMATION: Reverse Primer

<400> SEQUENCE: 3
cggctaccgt tacatc                                                         16

<210> SEQ ID NO 4
<211> LENGTH: 16
<212> TYPE: DNA
<213> ORGANISM: Artificial Sequence
<220> FEATURE:
<223> OTHER INFORMATION: Probe favourable

<400> SEQUENCE: 4
cgtaggacgg cgttat                                                         16

<210> SEQ ID NO 5
<211> LENGTH: 17
<212> TYPE: DNA
<213> ORGANISM: Artificial Sequence
<220> FEATURE:
<223> OTHER INFORMATION: Probe recurrent

<400> SEQUENCE: 5
tcgtaggacg gtgttat                                                        17

<210> SEQ ID NO 6
<211> LENGTH: 1911
<212> TYPE: DNA
<213> ORGANISM: Solanum habrochaites

<400> SEQUENCE: 6
atggccaccc agtgttatga ccccgaaaac tccgcctctc attacacatt cctcccggat         60
caacccgatt ccggccaccg gaagtccctt aaaatcttct ccggcatttt cctctccgtt        120
ttccttttgc tttctgtagc cttytttccg atcctcaaca accagtcacc ggacttgcga        180
atcgactccc gttcgccggc gccgccgtca gaggtgtttt ctcagggagt ctctgataaa        240
acttttcgag atgtagccgg tgctagtcac gtttcttatg cgtggtccaa tgctatgctt        300
agctggcaaa gaacggctta ccattttcaa cctcagaaaa attggatgaa cgatcctaat        360
ggaccattgt atcacaaggg atggtaccac cttttttatc aatacaatcc agattcggct        420
atttggggga atatcacatg gggccatgct gtatccaagg acttgatcca ctggctctac        480
ttgccttttg ccatggttcc tgatcagtgg tatgatatta cggtgtctg acagggtcc         540
gctaccatcc tacccgatgg tcagatcatg atgctttata ccggtgacac ggatgattat        600
gtacaagtgc aaaatcttgc gtaccccgcc aacttatctg atcctctcct tctagactgg        660
gtcaagtaca aggcaacccc ggttctggtt cctccacccg gcattgggt caaggacttt        720
agagacccga ctactgcttg gaccggaccg caaaatgggc aatggctgtt aacaatcggg        780
tccaagattg gtaaaacggg tattgcactt gtttatgaaa cttccaactt cacaagcttt        840
aagctattgg atggagtgct gcatgcggtt ccgggtacgg gtatgtggga gtgtgtggac        900
ttttacccgg tgtctactaa aaaaacaaat gggttggaca catcatataa cgggccgggt        960
gtaaagcatg tgttaaaagc aagtttagat gacaataagc aagatcatta tgctattggt       1020
acgtatgact tgacaaagaa caaatggaca cccgacaacc cggaattkga ttgtggaatt       1080
gggttgagac tagactatgg gaaatattat gcatcaaaga ctttttatga cccgaagaaa       1140
caacgaagag tactgtgggg atggattggg gaaactgaca gtgaatctgc tgacctgcag       1200
aagggatggg catctgtaca gagtattcca aggacagtgc tttacgacaa gaagacaggg       1260

-continued

```
acacatctac ttcagtggcc agtggaagaa attgaaagct taagagtggg tgatcctatt    1320
gttaagcaag tcgatcttca accaggctca attgagctac tccgtgttga ctcagctgca    1380
gagttggata tagaagtctc atttgaagtg dacaaagtcg cgcttcaggg aataattgaa    1440
gcagatcatg ttggtttcag ttgctctact agtggaggtg ctgctagcag aggcattttg    1500
ggaccgtttg gtgtcatagt gattgctgat caaacgctat ctgagctaac gccagtttac    1560
ttctacattt ctaaaggagc tgatggtcgt gcagagactc acttctgtgc tgatcaaact    1620
agatcctcag aggctccggg agttggtaaa caagtttatg gtagttcagt acctgtgttg    1680
gacggtgaaa acattcaat gagattattg gtggatcact caattgtgga gagctttgct    1740
caaggaggaa gaacagtcat agcatcgcga atttacccaa caaaggcagc aaatggagca    1800
gcacgactct tcgttttcaa caatgctaca ggggctagcg ttactgcctc cgtcaagatt    1860
tggtcacttg actcagctaa tattcgatcc ctcccttgc aagacttgta a               1911

<210> SEQ ID NO 7
<211> LENGTH: 24
<212> TYPE: DNA
<213> ORGANISM: Artificial Sequence
<220> FEATURE:
<223> OTHER INFORMATION: Forward primer

<400> SEQUENCE: 7
agtctcaacc caattccaca atcc                                              24

<210> SEQ ID NO 8
<211> LENGTH: 19
<212> TYPE: DNA
<213> ORGANISM: Artificial Sequence
<220> FEATURE:
<223> OTHER INFORMATION: Reverse primer

<400> SEQUENCE: 8
ggttccgggt acgggtatg                                                    19

<210> SEQ ID NO 9
<211> LENGTH: 15
<212> TYPE: DNA
<213> ORGANISM: Artificial Sequence
<220> FEATURE:
<223> OTHER INFORMATION: Probe favourable

<400> SEQUENCE: 9
aattccgggt tgtcg                                                        15

<210> SEQ ID NO 10
<211> LENGTH: 16
<212> TYPE: DNA
<213> ORGANISM: Artificial Sequence
<220> FEATURE:
<223> OTHER INFORMATION: Probe recurrent

<400> SEQUENCE: 10
aattccgggt tatcgg                                                       16

<210> SEQ ID NO 11
<211> LENGTH: 22
<212> TYPE: DNA
<213> ORGANISM: Artificial Sequence
<220> FEATURE:
<223> OTHER INFORMATION: Forward primer
```

```
<400> SEQUENCE: 11
tgctttctgt agccttcttt cc                                              22

<210> SEQ ID NO 12
<211> LENGTH: 21
<212> TYPE: DNA
<213> ORGANISM: Artificial Sequence
<220> FEATURE:
<223> OTHER INFORMATION: Reverse primer

<400> SEQUENCE: 12
tgccagctaa gcatagcatt g                                               21

<210> SEQ ID NO 13
<211> LENGTH: 16
<212> TYPE: DNA
<213> ORGANISM: Artificial Sequence
<220> FEATURE:
<223> OTHER INFORMATION: Probe favourable

<400> SEQUENCE: 13
cggacttgcg aatcga                                                     16

<210> SEQ ID NO 14
<211> LENGTH: 16
<212> TYPE: DNA
<213> ORGANISM: Artificial Sequence
<220> FEATURE:
<223> OTHER INFORMATION: Probe recurrent

<400> SEQUENCE: 14
cggacttgca aatcga                                                     16

<210> SEQ ID NO 15
<211> LENGTH: 527
<212> TYPE: DNA
<213> ORGANISM: Solanum lycopersicum

<400> SEQUENCE: 15
atgagaaatt tattccccat attgatgtta ctcactaatt tgtcactcaa catcgataac      60
aacaacaaca acaacatcat acgcgcaacg tgtagggaga ctccatacta ctccctatgt     120
ctctcagtcc tagaatccga tccacgtagc tacaaggctg agggtagtga tgatataacc     180
accctaggcc tcatcatggt ggatgcggtg aaatcaaagt ctatagaaat aatgaaaaag     240
ctaaaagagc tagagaaatc gaaccctgag tggcgggtcc cacttaacca gtgttacatg     300
gtgtataaca ccgtcctacg agccgatgta acggtagccg ttgaagcctt gaagaggggt     360
gtccctaaat ttgctgaaga tggtatggat gatgttgttg tagaagcaca aacttgtgag     420
tttagtttta attattataa taaatcggat tttccaattt ctaatatgag taaggacata     480
gttgaactct caaaagtcgc taaatccata attagaatgt tattatg                   527

<210> SEQ ID NO 16
<211> LENGTH: 527
<212> TYPE: DNA
<213> ORGANISM: Solanum pennellii LA0716

<400> SEQUENCE: 16
atgagaaatt tattccccat attgatgtta atcactaatt tatcactcaa caacgataac      60
aacaacaaca acaacatcat acgcgcaacg tgtagggaga ctccatacta ctccctatgt     120
ctctcaatcc tagaatccga tccacgtagc tacgaggctg agggtagtga tgatataact     180
```

```
acccctaggcc tcatcatggt ggatgcagtg aaatcaaagt ctatagaaat aatgaaaaag    240
ctaaaagagc tagaaaaatc gaaccctgag tggcgggtcc cacttaacca gtgttacatg    300
gtgtataaca ccgtcctacg agccgatgta acggtagccg ttgaagcctt gaagaggggt    360
gtccctaaat ttgctgaaga tggtatggat gatgttgttg tagaagcaca aacttgtgag    420
tttagtttta attattataa taaatcggat tttccaattt ctaatatgag taaggacata    480
attgaactct caaaagtcgc taaatccata attagaatgt tattatg                  527

<210> SEQ ID NO 17
<211> LENGTH: 527
<212> TYPE: DNA
<213> ORGANISM: Solanum cheesmaniae LA0429

<400> SEQUENCE: 17
atgagaaatt tattccccat attgatgtta ctcactaatt tgtcactcaa catcgataac    60
aacaacaaca caacatcat acgcgcaacg tgtagggaga ctccatacta ctccctatgt    120
ctctcagtcc tagaatccga tccacgtagc tacaaggctg agggtagtga tgatataacc    180
accctaggcc tcatcatggt ggatgcggtg aaatcaaagt ctatagaaat aatgaaaaag    240
ctaaaagagc tagagaaatc gaaccctgag tggcgggtcc cacttaacca gtgttacatg    300
gtgtataaca ccgtcctacg agccgatgta acggtagccg ttgaagcctt gaagaggggt    360
gtccctaaat ttgctgaaga tggtatggat gatgttgttg tagaagcaca aacttgtgag    420
tttagtttta attattataa taaatcggat tttccaattt ctaatatgag taaggacata    480
gttgaactct caaaagtcgc taaatccata attagaatgt tattatg                  527

<210> SEQ ID NO 18
<211> LENGTH: 527
<212> TYPE: DNA
<213> ORGANISM: Solanum pimpinellifolium LA1589

<400> SEQUENCE: 18
atgagaaatt tattccccat attgatgtta ctcactaatt tgtcactcaa catcgataac    60
aacaacaaca caacatcat acgcgcaacg tgtagggaga ctccatacta ctccctatgt    120
ctctcagtcc tagaatccga tccacgtagc tacaaggctg agggtagtga tgatataacc    180
accctaggcc tcatcatggt ggatgcggtg aaatcaaagt ctatagaaat aatgaaaaag    240
ctaaaagagc tagagaaatc gaaccctgag tggcgggtcc cacttaacca gtgttacatg    300
gtgtataacg ccgtcctacg agccgatgta acggtagccg ttgaagcctt gaagaggggt    360
gtccctaaat ttgctgaaga tggtatggat gatgttgttg tagaagcaca aacttgtgag    420
tttagtttta attattataa taaatcggat tttccaattt ctaatatgag taaggacata    480
gttgaactct caaaagttgc taaatccata attagaatgt tattatg                  527

<210> SEQ ID NO 19
<211> LENGTH: 1911
<212> TYPE: DNA
<213> ORGANISM: Solanum peruvianum KY565130

<400> SEQUENCE: 19
atggccactc agtgttatga ccccgaaaac tccgcctctc attacacatt cctcccggat    60
caacccgatt ccggccaccg gaagtccctt aaaatcatct ccggcatttt cctctccgtt    120
ttccttttgc tttctgtagc cttctttccg atcctcaaca accagtcacc ggacttgcaa    180
```

-continued

```
atcgactccc gttcgccggc gccgccgtca agaggtgttt ctcagggagt ctccgataaa      240
acttttcgag atgtagccgg tgctagtcac gtttcttatg cgtggtccaa tgctatgctt      300
agctggcaaa gaacggctta ccattttcaa cctcaaaaaa attggatgaa cgatcctaat      360
ggaccattgt atcacaaggg atggtaccac ctttttttatc aatacaatcc agattcagct     420
atttggggaa atatcacatg gggccatgct gtatccaagg acttgatcca ctggctctac      480
ttgccttttg ccatggttcc tgatcaatgg tatgatatta cggtgtctg gacagggtcc       540 gctaccatcc tacccgatgg tcagatcatg atgctttata ccggtgacac tgatgattat      600
gtgcaagtgc aaaatcttgc gtaccccgcc aacttatctg atcctctcct tctagactgg      660
gtcaagtaca aaggcaaccc ggttctggtt cctccacccg gcattggtgt caaggacttt      720
agggacccga ctactgcttg gaccggaccg caaaatgggc aatggctgtt aacaatcggg      780
tctaagattg gtaaagcggg tattgcactt gtttatgaaa cttccaactt cacaagcttt      840
aagctattgg atggagtgct gcatgcggtt ccgggtacgg gtatgtggga gtgtgtggac      900
ttttacccgg tatctactaa aaaaacaaat gggttggaca catcatataa cgggccgggt      960
gtaaagcatg tgttaaaagc aagtttagat ggcaataagc aagatcatta tgctattggt     1020
acgtatgact tggcaaagaa caaatggaca cccgataacc cggaattgga ttgtggaatt     1080
gggttgagac tagactatgg gaaatattat gcatcaaaga cttttttatga cccgaagaaa    1140 gaacgaagag tactgtgggg atggattggg gaaactgaca gtgaatctgc tgacctgcag     1200
aagggatggg catctgtaca gagtattcca aggacagtgc tttacgacaa taagacaggg     1260
acacatctac ttcagtggcc agtggaagaa attgaaagct taagagtggg tgatcctatt     1320
gttaaggaag tcgatcttca accaggctca attgagctac tccgtgttga ctcagctgca     1380
gagttggata tagaagtctc atttgaagtg acaaagtcg cgcttcaggg aataattgaa      1440
gaagatcatg taggtttcag ttgctctact agtggaggtg ctgctagcag aggcattttg     1500
ggaccatttg tgtcatagt aattgctgat caaacgctat ctgaattaac gccagtttac      1560
ttctacattt ctaaaggagc tgatggtcgt gcagagactc acttctgtgc tgatcaaact     1620
agatcctcag aggctccggg agttggtaaa caagtttatg gtagttcagt acctgtgttg     1680
gacggtgaaa acactcaat gagattattg gtggatcact caattgtgga gagctttgct     1740
caaggaggaa gaacagtcat aacatcgcga atttacccaa caaaggcagt agatggagca    1800
gcacgactct tcgttttcaa caatgccaca ggggctagcg ttactgcctc cgtcaagatt    1860
tggtcaattg agtcagctaa tattcgatcc ttcccttttgc aagacttgta a             1911
```

<210> SEQ ID NO 20
<211> LENGTH: 1911
<212> TYPE: DNA
<213> ORGANISM: Solanum pennellii XM015214462

<400> SEQUENCE: 20

```
atggccaccc agtgttatga ccccgaaaac tccgcctctc actacacatt cctcccggat       60
caacccgatt ccggccaccg gaagtccctt aaaatcatct ccggcatttt cctctccgtt      120
ttccttttgc tttctgtagc cttctttccg atcctcaaca accagtcacc ggacttgcaa      180
atcgactccc gttcgccggc gccgccgtca agaggtgttt ctcagggagt ctccgataaa      240
acttttcgag atgtagccgg ggctagtcac gtttcttatg cgtggtccaa tgctatgctt      300
agctggcaaa gaactgctta ccattttcaa cctcaaaaaa attggatgaa cgatcctaat      360
ggaccattgt atcacaaggg atggtaccac ctttttttatc aatacaatcc agattcagct     420
```

```
atttggggaa atatcacatg gggccatgct gtatccaagg acttgatcca ctggctctac      480
ttgccttttg ccatggttcc tgatcaatgg tatgatatta cgtgtgtctg gactgggtcc      540
gctaccatcc tacccgatgg tcagatcatg atgctttata ccggtgacac tgatgattat      600
gtgcaagtgc aaaatcttgc gtaccccgcc aacttatctg atcctctcct tctagactgg      660
gtcaagtaca aaggcaaccc ggttctggtt cctccacccg gcattgctgt caaggacttt      720
agagacccga ctactgcttg gaccggaccg caaaatgggc aatggctgtt aacaatcggg      780
tctaagattg gtaaaacggg tattgcactt gtttatgaaa cttccaactt cacaagcttt      840
aagctattgg atggagtgct gcatgcggtt ccgggtacgg gtatgtggga gtgtgtggac      900
ttttacccgg tatctactaa aaaaacaaat gggttggaca catcatataa cgggccgggt      960
gtaaagcatg ttttaaaagc aagtttagat gacaataagc aagatcatta tgctattggt     1020
acgtatgact tgacaaagaa caaatggacg cccgataacc cggaattgga ttgtggaatt     1080
gggttgagac tagactatgg gaaatattat gcatcaaaga cttttttatga cccgaagaaa     1140 caacgaagag tactgtgggg atggattggg gaaactgaca gtgaatctgc tgacctgcag     1200
aagggatggg catctgtaca gagtattcca aggacagtgc tttacgacaa gaagacaggg     1260
acacatctac ttcagtggcc agtggaagaa attgaaagct aagagtgggg tgatcctatt     1320
gttaagcaag tcgatcttca accaggctca attgagctac tccgtgttga ctcagctgca     1380
gagttggata tagaagtctc atttgaagtg acaaagtcg cgcttcaggg aataattgaa       1440
gcagatcatg taggtttcag ttgctctact agtggaggtg ctgctagcag aggcattttg     1500
ggaccatttg gtgtcatagt aattgctgat caaacgctat ctgagctaac gccagtttac     1560
ttctacattt ctaaaggagc tgatggtcgt gcagagactc acttctgtgc tgatcaaact     1620
agatcctcag aggctccggg agttggtaaa caagtttatg gtagttcagt acctgtgttg     1680
gacggtgaaa aacactcaat gagattattg gtggatcact caattgtgga gagctttgct     1740
caaggaggaa gaacagtcat aacatcgcga atttacccaa caaaggcagt aaatggagca     1800
gcacgactct tcgttttcaa caatgccaca ggggctagcg ttactgcctc cgtcaagatt     1860
tggtcacttg agtcagctaa tattcgatcc ttcccttttgc aagacttgta a              1911
```

<210> SEQ ID NO 21
<211> LENGTH: 1908
<212> TYPE: DNA
<213> ORGANISM: Solanum chmielewskii KY565126

<400> SEQUENCE: 21

```
atggccactc agtgttatga ccccgaaaac tccgcctctc attacacatt actcccggat       60
caacccgatt ccggccaccg gaagtccctt aaaatcatct ccggcatttt cctctccgtt      120
ttccttttgc tttgtgtagc cttctttccg atcctcaaca accagtcacc ggacttgcaa      180
atcgactccc gttcgccggc gccgccgtca agaggtgttt ctcagggagt ctccgataaa      240
acttttcgag atgtagccgg tgctagtcac gtttcttatg cgtggtccaa tgctatgctt      300
agctggcaaa gaacggctta ccattttcaa cctcaaaaaa attggatgaa cgatcctaat      360
ggaccattgt atcacaaggg atggtaccac cttttttatc aatacaatcc agattcagct      420
atttggggaa atatcacatg gggccatgct gtatccaagg acttgatcca ctggctctac      480
ttgccttttg tcatggttcc tgatcaatgg tatgatatta atggtgtctg gactgggtcc      540
gctaccatcc tacccgatgg tcagatcatg atgctttata ccggtgacac tgatgattat      600
```

```
gtgcaagtgc aaaatcttgc gtaccccgcc aacttatctg atcctctcct tctagactgg      660
gtcaagtaca aaggcaaccc ggttctggtt cctccacccg gcattggggt caaggacttt      720
agagacccga ctactgcttg gaccggaccg caaaatgggc aatggctgtt aacaatcggg      780
tctaagattg gtaaaacggg tgttgcactt gtttatgaaa cttccaactt cacaagcttt      840
aagctattgg atggagtgct gcatgcggtt ccgggtacgg gtatgtggga gtgcgtggac      900
ttttacccgg tatctactaa aaaaacaaat gggttggaca catcatataa cgggccgggt      960
gtaaagcatg tgttaaaagc aagtttagat gacaataagc aagatcatta tgctattggg     1020
acgtatgact ggcaaagaa caaatggaca cccgataacc cggaattgga ttgtggaatt       1080
gggttgagac tagactatgg gaaatattat gcaccaaaga cttttatga cccgaagaaa       1140 gaacgaagag tactgtgggg atggattggg gaaactgaca gtgaatctgc tgacctgcag      1200
aagggatggg catctgtaag tattccaagg acagtgcttt acgacaagaa gacagggaca      1260
catctacttc agtggccagt ggaagaaatt gaaagcttaa gagtgggtga tcctattgtt      1320
aagcaagtcg atcttcaacc aggctcaatt gagctactcc gtgttgactc agctgcagag     1380
ttggatatag aagtctcatt tgaagtggac aaagtcgcgc ttcagggaat aattgaagca     1440
gatcatgtag gtttcagttg ctctactagt ggaggtgctg ctagcagagg cattttggga     1500
ccatttggtg tcatagtaat tgctgatcaa acgctatctg agctaacgcc agtttacttc      1560
tacatttcta aaggagctga tggtcgtgca gagactcact tctgtgctga tcaaactaga     1620
tcctcagagg ctccgggagt tggtaaacaa gtttatggta gttcagtacc tgtgttggac      1680
ggtgaaaaac attcaatgag attattggtg gatcactcaa ttgtggagag ctttgctcaa      1740
ggaggaagaa cagtcataac atcgcgaatt tacccaacaa aggcagtaaa tggagcagca      1800
cgactctttg ttttcaacaa tgccacaggg gctagcgtta ctgcctccgt caagatttgg      1860
ccacttgagt cagctaatat tcgatccttc cctttgcaag acttgtaa                    1908

<210> SEQ ID NO 22
<211> LENGTH: 1911
<212> TYPE: DNA
<213> ORGANISM: Solanum lycopersicum NM001247914

<400> SEQUENCE: 22
atggccactc agtgttatga ccccgaaaac tccgcctctc gttacacatt actcccggat       60
caacccgatt ccgccaccg gaagtccctt aaaatcatct ccggcatttt cctctccgtt      120
ttccttttgc tttctgtagc cttctttccg atcctcaaca accagtcacc ggacttgcaa      180
atcgactccc gttcgccggc gccgccgtca agaggtgttt ctcagggagt ctccgataaa      240
acttttcgag atgtagccgg tgctagtcac gtttcttatg cgtggtccaa tgctatgctt      300
agctggcaaa gaacggctta ccattttcaa cctcaaaaaa attggatgaa cgatcctaat      360
ggaccattgt atcacaaggg atggtaccac cttttttatc aatacaatcc agattcagct      420
atttggggaa atatcacatg gggccatgct gtatccaagg acttgatcca ctggctctac      480 ttgcctttttg ccatggttcc tgatcaatgg tatgatatta cggtgtctg dacagggtcc     540 gctaccatcc tacccgatgg tcagatcatg atgctttata ccggtgacac tgatgattat      600
gtgcaagtgc aaaatcttgc gtaccccgcc aacttatctg atcctctcct tctagactgg      660
gtcaagttca aaggcaaccc ggttctggtt cctccacccg gcattggtgt caaggacttt      720
agagacccga ctactgcttg gaccggacca caaaatgggc aatggctgtt aacaatcggg      780
tctaagattg gtaaaacggg tgttgcactt gtttatgaaa cttccaactt cacaagcttt      840
```

```
aagctattgg atggagtgct gcatgcggtt ccgggtacgg gtatgtggga gtgtgtggac      900 tttttacccgg tatctactaa aaaaacaaac gggttggaca catcatataa cgggccgggt     960
gtaaagcatg tgttaaaagc aagtttagat gacaataagc aagatcatta tgctattggt    1020
acgtatgact tgggaaagaa caaatggaca cccgataacc cggaattgga ttgtggaatt    1080
gggttgagac tagactatgg gaaatattat gcatcaaaga cttttttatga cccgaagaaa   1140 gaacgaagag tactgtgggg atggattggg gaaactgaca gtgaatctgc tgacctgcag    1200
aagggatggg catctgtaca gagtattcca aggacagtgc tttacgacaa gaagacaggg   1260
acacatctac ttcagtggcc agtggaagaa attgaaagct taagagtggg tgatcctact    1320
gttaagcaag tcgatcttca accaggctca attgagctac tccgtgttga ctcagctgca    1380
gagttggata tagaagcctc atttgaagtg gacaaagtcg cgcttcaggg aataattgaa   1440
gcagatcatg taggtttcag ttgctctact agtggaggtg ctgctagcag aggcattttg    1500
ggaccatttg tgtcatagt aattgctgat caaacgctat ctgagctaac gccagtttac     1560
ttttacattt ctaaaggagc tgatggtcgt gcagagactc acttctgtgc tgatcaaact    1620
agatcctctg aggctccggg agttggtaaa caagtttatg gtagttcagt acctgtgttg    1680
gacggtgaaa acattcaat gagattattg gtggatcact caattgtgga gagctttgct     1740
caaggaggaa gaacagtcat aacatcgcga atttacccaa caaaggcagt aaatggagca    1800
gcacgactct ttgttttcaa caatgccaca ggggctagcg ttactgcctc cgtcaagatt    1860
tggtcacttg agtcagctaa tattcaatcc ttccctttgc aagacttgta a             1911

<210> SEQ ID NO 23
<211> LENGTH: 1911
<212> TYPE: DNA
<213> ORGANISM: Solanum lycopersicum var. cerasiforme GU784870

<400> SEQUENCE: 23
atggccactc agtgttatga ccccgaaaac tccgcctctc gttacacatt actcccggat      60
caacccgatt ccggccaccg gaagtcccct aaaatcatct ccggcatttt cctctccgtt    120
ttccttttgc tttctgtagc cttctttccg atccccaaca accagtcacc ggacttgcaa    180
atcgactccc gttcgccggc gccgccgtca agaggtgttt ctcagggagt ctccgataaa    240
acttttcgag atgtagccgg tgctagtcac gtttcttatg cgtggccaa tgctatgctt     300 agctggcaaa gaacggctta ccatttttcaa cctcaaaaaa attggatgaa cgatcctaat     360
ggaccattgt atcacaaggg atggtaccac cttttttatc aatacaatcc agattcagct    420
atttggggaa atatcacatg gggccatgct gtatccaagg acttgatcca ctggctctac     480
ttgccttttg ccatggttcc tgatcaatgg tatgatatta cggtgtctg gacagggtcc     540 gctaccatcc tacccgatgg tcagatcatg atgctttata ccggtgacac tgatgattat    600
gtgcaagtgc aaaatcttgc gtaccccgcc aacttatctg atcctctcct tctagactgg    660
gtcaagttca aggcaacccc ggttctggtt cctccacccg gcattggtgt caaggacttt    720
agagacccga ctactgcttg gaccggacca caaaatgggc aatggctgtt aacaatcggg     780
tctaagattg gtaaaacggg tgttgcactt gtttatgaaa cttccaactt cacaagcttt     840
aagctattgg atggagtgct gcatgcggtt ccgggtacgg gtatgtggga gtgtgtggac      900 tttttacccgg tatctactaa aaaaacaaac gggttggaca catcatataa cgggccgggt     960
gtaaagcatg tgttaaaagc aagtttagat gacaataagc aagatcatta tgctattggt    1020
```

| | |
|---|---|
| acgtatgact tgggaaagaa caaatggaca cccgataacc cggaattgga ttgtggaatt | 1080 |
| gggttgagac tagactatgg gaaatattat gcatcaaaga cttttttatga cccgaagaaa | 1140 |
| gaacgaagag tactgtgggg atggattggg gaaactgaca gtgaatctgc tgacctgcag | 1200 |
| aagggatggg catctgtaca gagtattcca aggacagtgc tttacgacaa gaagacaggg | 1260 |
| acacatctac ttcagtggcc agtggaagaa attgaaagct taagagtggg tgatcctact | 1320 |
| gttaagcaag tcgatcttca accaggctca attgagctac tccgtgttga ctcagctgca | 1380 |
| gagttggata tagaagcctc atttgaagtg gacaaagtcg cgcttcaggg aataattgaa | 1440 |
| gcagatcatg taggtttcag ttgctctact agtggaggtg ctgctagcag aggcattttg | 1500 |
| ggaccatttg gtgtcatagt aattgctgat caaacgctat ctgagctaac gccagtttac | 1560 |
| ttttacattt ctaaaggagc tgatggtcgt gcagagactc acttctgtgc tgatcaaact | 1620 |
| agatcctctg aggctccggg agttggtaaa caagtttatg gtagttcagt acctgtgttg | 1680 |
| gacggtgaaa acattcaat gagattattg gtggatcact caattgtgga gagctttgct | 1740 |
| caaggaggaa gaacagtcat aacatcgcga atttacccaa caaggcagt aaatggagca | 1800 |
| gcacgactct ttgttttcaa caatgccaca ggggctagcg ttactgcctc cgtcaagatt | 1860 |
| tggtcacttg agtcagctaa tattcaatcc ttcccttttgc aagacttgta a | 1911 |

<210> SEQ ID NO 24
<211> LENGTH: 1911
<212> TYPE: DNA
<213> ORGANISM: Solanum cheesmaniae KY565124

<400> SEQUENCE: 24

| | |
|---|---|
| atggccactc agtgttatga ccccgaaaac tccgcctctc gttacacatt actcccggat | 60 |
| caacccgatt ccggccaccg gaagtccctt aaaatcatct ccggcatttt cctctccgtt | 120 |
| ttccttttgc tttctgtagc cttctttccg atcctcaaca accagtcacc ggacttgcaa | 180 |
| atcgactccc gttcgccggc gccgccgtca agaggtgttt tcagggagt ctccgataaa | 240 |
| acttttcgag atgtagccgg tgctagtcac gtttcttatg cgtggtccaa tgctatgctt | 300 |
| agctggcaaa gaacggctta ccattttcaa cctcaaaaaa attggatgaa cgatcctaat | 360 |
| ggaccattgt atcacaaggg atggtaccac cttttttatc aatacaatcc agattcagct | 420 |
| atttggggaa atatcacatg gggccatgct gtatccaagg acttgatcca ctggctctac | 480 |
| ttgccttttg ccatggttcc tgatcaatgg tatgatatta acggtgtctg gacagggtcc | 540 |
| gctaccatcc tacccgatgg tcagatcatg atgctttata ccggtgacac tgatgattat | 600 |
| gtgcaagtgc aaaatcttgc gtaccccgcc aacttatctg atcctctcct tctagactgg | 660 |
| gtcaagttca aggcaaccc ggttctggtt cctccacccg gcattggtgt caaggacttt | 720 |
| agagacccga ctactgcttg gaccggacca caaaatgggc aatggctgtt aacaatcggg | 780 |
| tctaagattg gtaaaacggg tgttgcactt gtttatgaaa cttccaactt cacaagcttt | 840 |
| aagctattgg atggagtgct gcatgcggtt ccgggtacgg gtatgtggga gtgtgtggac | 900 |
| ttttacccgg tatctactaa aaaacaaac gggttggaca catcatataa cgggccgggt | 960 |
| gtaaagcatg tgttaaaagc aagtttagat gacaataagc aagatcatta tgctattggt | 1020 |
| acgtatgact tgggaaagaa caaatggaca cccgataacc cggaattgga ttgtggaatt | 1080 |
| gggttgagac tagactatgg gaaatattat gcatcaaaga cttttttatga cccgaagaaa | 1140 |
| gaacgaagag tactgtgggg atggattggg gaaactgaca gtgaatctgc tgacctgcag | 1200 |
| aagggatggg catctgtaca gagtattcca aggacagtgc tttacgacaa gaagacaggg | 1260 |

```
acacatctac ttcagtggcc agtggaagaa attgaaagct taagagtggg tgatcctact    1320
gttaagcaag tcgatcttca accaggctca attgagctac tccgtgttga ctcagctgca    1380
gagttggata tagaagcctc atttgaagtg acaaagtcg cgcttcaggg aataattgaa    1440
gcagatcatg taggttttcag ttgctctact agtggaggtg ctgctagcag aggcattttg    1500
ggaccatttg gtgtcatagt aattgctgat caaacgctat ctgagctaac gccagtttac    1560
ttttacattt ctaaaggagc tgatggtcgt gcagagactc acttctgtgc tgatcaaact    1620
agatcctctg aggctccggg agttggtaaa caagtttatg gtagttcagt acctgtgttg    1680
gacggtgaaa acattcaat gagattattg gtggatcact caattgtgga gagctttgct    1740
caaggaggaa gaacagtcat aacatcgcga atttacccaa caaaggcagt aaatggagca    1800
gcacgactct tgttttcaa caatgccaca ggggctagcg ttactgcctc cgtcaagatt    1860
tggtcacttg agtcagctaa tattcaatcc ttccctttgc aagacttgta a    1911
```

<210> SEQ ID NO 25
<211> LENGTH: 1911
<212> TYPE: DNA
<213> ORGANISM: Solanum pimpinellifolium Z12026

<400> SEQUENCE: 25

```
atggccactc agtgttatga ccccgaaaac tccgcctctc gttacacatt actcccggat      60
caacccgatt ccggccaccg gaagtccctt aaaatcatct ccggcatttt cctctccgtt     120
ttccttttgc tttctgtagc cttctttccg atcctcaaca accagtcacc ggacttgcaa     180
atcgactccc gttcgccggc gccgccgtca agaggtgttt ctcagggagt ctccgataaa     240
acttttcgag atgtagccgg tgctagtcac gtttcttatg cgtggtccaa tgctatgctt     300
agctggcaaa gaacggctta ccattttcaa cctcaaaaaa attggatgaa cgatcctaat     360
ggaccattgt atcacaaggg atggtaccac ctttttttatc aatacaatcc agattcagct     420
atttggggaa atatcacatg gggccatgct gtatccaagg acttgatcca ctggctctac     480
ttgccttttg ccatggttcc tgatcaatgg tatgatatta cggtgtctg gacagggtcc     540
gctaccatcc tacccgatgg tcagatcatg atgctttata ccggtgacac tgatgattat     600
gtgcaagtgc aaaatcttgc gtaccccgcc aacttatctg atcctctcct tctagactgg     660
gtcaagttca aaggcaaccc ggttctggtt cctccacccg gcattggtgt caaggacttt     720
agagacccga ctactgcttg gaccggacca caaaatgggc aatggctgtt aacaatcggg    780
tctaagattg gtaaaacggg tgttgcactt gtttatgaaa cttccaactt cacaagcttt    840
aagctattgg atggagtgct gcatgcggtt ccgggtacgg gtatgtggga gtgtgtggac    900
ttttacccgg tatctactaa aaaaacaaac gggttggaca catcatataa cgggccgggt    960
gtaaagcatg tgttaaaagc aagtttagat gacaataagc aagatcatta tgctattggt   1020
acgtatgact gggaaagaa caaatggaca cccgataacc cggaattgga ttgtggaatt   1080
gggttgagac tagactatgg gaaatattat gcatcaaaga cttttatgag cccgaagaaa   1140
gaacgaagag tactgtgggg atggattggg gaaactgaca gtgaatctgc tgacctgcag   1200
aagggatggg catctgtaca gagtattcca aggacagtgc tttacgacaa gagacaggg    1260
acacatctac ttcagtggcc agtggaagaa attgaaagct taagagtggg tgatcctact   1320
gttaagcaag tcgatcttca accaggctca attgagctac tccgtgttga ctcagctgca   1380
gagttggata tagaagcctc atttgaagtg acaaagtcg cgcttcaggg aataattgaa    1440
```

```
gcagatcatg taggtttcag ttgctctact agtggaggtg ctgctagcag aggcattttg    1500
ggaccatttg gtgtcatagt aattgctgat caaacgctat ctgagctaac gccagtttac    1560
ttttacattt ctaaaggagc tgatggtcgt gcagagactc acttctgtgc tgatcaaact    1620
agatcctctg aggctccggg agttggtaaa caagtttatg gtagttcagt acctgtgttg    1680
gacggtgaaa aacattcaat gagattattg gtggatcact caattgtgga gagctttgct    1740
caaggaggaa gaacagtcat aacatcgcga atttacccaa caaaggcagt aaatggagca    1800
gcacgactct ttgttttcaa caatgccaca ggggctagcg ttactgcctc cgtcaagatt    1860
tggtcacttg agtcagctaa tattcaatcc ttccctttgc aagacttgta a             1911
```

TOMATO PLANT PRODUCING FRUITS WITH MODIFIED SUGAR CONTENT

RELATED APPLICATION INFORMATION

This application claims priority under 35 U.S.C. § 371 from International Application No. PCT/EP2019/077627 filed 11 Oct. 2019, which claims priority from EP Application No. 18200806.0 filed 16 Oct. 2018, EP Application No. 18207600.0 filed 21 Nov. 2018, and EP Application No. 19152831.4 filed 21 Jan. 2019, the contents of which are incorporated herein by reference in their entirety.

STATEMENT REGARDING ELECTRONIC SUBMISSION OF A SEQUENCE LISTING

A Sequence Listing in ASCII text format, submitted under 37 C.F.R. § 1.821, entitled eolf-othd-000004.txt, 26 kb in size, generated on Oct. 11, 2019 and filed via EFS-Web is provided in lieu of a paper copy. This Sequence Listing is hereby incorporated by reference into the specification for its disclosures.

FIELD OF THE INVENTION

The present invention relates to novel tomato plants producing fruits displaying a modified sugar content, particularly displaying an increased sucrose content. The present invention also relates to seeds and parts of said plants, for example fruits. The present invention further relates to methods of making and using such seeds and plants. The present invention also relates to a novel sucrose modifier SucMod allele, which, when combined with a sucrose accumulation TIV allele derived from a green-fruited wild tomato accession, significantly alters the proportion of sugar stored in the fruit, confers increased fruit sucrose content at the expense of hexose sugars and results in a fruit with a distinctive flavor.

BACKGROUND OF THE INVENTION

Tomato is a well-known source of vitamins, minerals and antioxidants, which make up essential components of a balanced healthy diet. It is also widely accepted that quality attributes such as colour, flavour and firm texture will strongly influence consumer choice in the purchase of this expensive and readily perishable crop fruit.

Soluble sugars form approximately half of the dry matter in the ripe tomato fruit and their levels strongly impact parameters by which fruit quality can be measured, such as fruit flavour, sweetness of taste, consumer preference, and total soluble solid content (Brix units). Traditionally, cultivated tomato varieties (*Solanum lycopersicum*) accumulate the hexose monosaccharides glucose and fructose, as do the other red-, orange- and yellow-fruited species, *Solanum cheesmanii* and *Solanum pimpinellifolium*, which form the Eulycopersicum subgroup. Conversely, they accumulate low levels of the fructose-glucose disaccharide sucrose. In contrast, the green-fruited wild species that make up the Eriopersicum group (*Solanum habrochaites* (previously *Lycopersicon hirsutum*), *Solanum chmielewskii*, *Solanum pennellii* and *Solanum peruvianum*) all accumulate the disaccharide sucrose as the major soluble sugar component (Davies, 1966; Manning and Maw, 1975).

This characteristic sugar accumulation was found to be due to a tomato vacuolar invertase enzyme (abbreviated to VA or TIV) that cleaves sucrose in the vacuole into its component hexoses. Previous studies have shown that a single locus (sucr) controls the trait of sucrose/hexose accumulation (Yelle et al., 1991; Chetelat et al., 1993; Klann et al., 1993, 1996; Hadas et al., 1995). The corresponding gene (TIV) encodes for a soluble acid invertase enzyme, which catalyses the hydrolysis of imported sucrose into hexose (Chetelat et al., 1993; Klann et al., 1993), and was mapped on chromosome 3 (Solyc03g083910). The green-fruited species exhibit a developmental cessation of TIV expression during maturation, triggering a decrease in protein level and enzymatic activity and ultimately allowing for sucrose to accumulate in the vacuole. In contrast, the red/orange/yellow-fruited species show a developmental rise in TIV expression and the resulting enzyme activity is responsible for the near total hydrolysis of sucrose into the hexose moieties glucose and fructose (Klann et al., 1993; Miron et al., 2002). Consequently, backcrossing a wild allele of TIV into a cultivated line can result in significantly increased sucrose levels and significantly reduced glucose and fructose levels when compared with the recurrent background line where no wild TIV allele is present (Hadas et al., 1995, table 2).

TIV expression and invertase activity thereof can also be modulated in a post-translational manner, via the proteinaceous invertase inhibitors. Indeed, research over the past few years has shown that control over invertase inhibitor expression can impact significantly on the in planta invertase hydrolysis and subsequently on sugar metabolism. For example, silencing of the cell wall invertase inhibitor (CIF) expression in developing tomato fruit led to an increase in apoplastic invertase activity (LIN5) and subsequent increase in sink activity and sugar accumulation in the fruit (Jin et al., 2009). Similarly, it was reported that a purified tomato vacuolar invertase (TIV) could be inhibited by the Solyc1299190 protein, indicating that the latter functions as an inhibitor of TIV (also called VIF; Tauzin et al., 2014; Qin et al., 2016).

However, the relative increase in sucrose content of cultivated tomato plants comprising a wild TIV allele (Klann et al., 1993, FIG. 2; Hadas et al., 1995, table 2, BC1F3 data) or an overexpressed VIF allele (Qin et al., 2016, FIG. 6D) seems to happen at the expense of total sugar content—which decreases, or is at best maintained at a similar level—and sucrose to hexose ratio—which rapidly peaks at below or around 0.50. There is therefore a need to further enhance the sucrose content of fruits of cultivated tomato plants while increasing the sucrose to hexose ratio and total sugar content and thus provide differentiating tomato plants and fruits to growers and consumers.

SUMMARY OF THE INVENTION

The present invention addresses the need for providing novel tomato plants producing fruits displaying a modified sugar content, particularly displaying an increased sucrose content.

In a first embodiment, the invention provides a cultivated tomato plant, preferably a cultivated *Solanum lycopersicum* plant, comprising:
  a) at least one copy of a sucrose modifier SucMod allele having at least 90% sequence identity with SEQ ID NO: 1, and;
  b) two copies of a sucrose accumulation TIV allele derived from a green-fruited wild tomato accession;
wherein said SucMod allele comprises a nucleotide G at a position which corresponds to position 310 of SEQ ID NO: 1, and/or a nucleotide T at a position which corresponds to position 498 of SEQ ID NO: 1; and, wherein said plant produces tomato fruit exhibiting an increased sucrose content compared with the same cultivated tomato plant lacking said SucMod and TIV alleles.

In a further embodiment of the invention, the SucMod allele is derived from *Solanum chmielewskii* or *Solanum pimpinelifolium*.

In a further embodiment of the invention, the SucMod allele comprises a nucleotide sequence of SEQ ID NO: 1.

In a further embodiment, the invention provides a plant according to any of the preceding embodiments, wherein said TIV allele has at least 98% sequence identity with SEQ ID NO: 6.

In a further embodiment, the invention provides a plant according to any of the preceding embodiments, wherein said TIV allele comprises a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide Tat a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

In a further embodiment, the invention provides a plant according to any of the preceding embodiments, wherein said TIV allele is derived from *Solanum habrochaites*.

In a further embodiment, the invention provides a plant according to any of the preceding embodiments, wherein said TIV allele comprises a nucleotide C at a position which corresponds to position 1056 of SEQ ID NO: 6; and/or a nucleotide G at a position which corresponds to position 179 of SEQ ID NO: 6.

In a further embodiment, the invention provides a plant according to any of the preceding embodiments, wherein said TIV allele comprises a nucleotide sequence of SEQ ID NO: 6.

In a further embodiment, the invention provides a plant according to any of the preceding embodiments, wherein said plant comprises two copies of the SucMod allele.

In a further embodiment, the invention provides a plant according to any of the preceding embodiments, wherein said TIV allele and said SucMod allele are obtainable from *Solanum lycopersicum* line TIPC18-61141, deposited with NCIMB on 20 Aug. 2018 under NCIMB Accession No. 43169.

In a further embodiment, the invention provides a plant according to any of the preceding embodiments, wherein said plant is an inbred, a dihaploid or a hybrid plant.

In a further embodiment, the invention provides a seed that produces a plant according to any of the preceding embodiments.

In a further embodiment, the invention provides a method for producing a cultivated tomato plant, preferably a cultivated *Solanum lycopersicum* plant, producing tomato fruits exhibiting increased sucrose content comprising the steps of
a) crossing a plant according to any of the preceding embodiments comprising at least one copy of a sucrose modifier SucMod allele and two copies of a sucrose accumulation TIV allele with a cultivated tomato plant lacking said SucMod and TIV alleles;

b) Selecting a progeny plant producing fruits exhibiting an increased sucrose content compared with the same cultivated tomato plant lacking said SucMod and TIV alleles;

wherein the selection of step b) is carried out by detecting a nucleotide G at a position which corresponds to position 310 of SEQ ID NO: 1 and/or a nucleotide T at a position which corresponds to position 498 of SEQ ID NO: 1; and, by detecting a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide Tat a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

In a further embodiment, the invention relates to the method of the preceding embodiment wherein the selection of step b) is carried out by further detecting a nucleotide C at a position which corresponds to position 1056 of SEQ ID NO: 6; and/or a nucleotide G at a position which corresponds to position 179 of SEQ ID NO: 6.

In a further embodiment, the invention relates to the method of any one of the preceding embodiments wherein the plant of step a) is *Solanum lycopersicum* line TIPC18-61141, deposited with NCIMB on 20 Aug. 2018 under NCIMB Accession No. 43169.

In a further embodiment, the invention provides a method for identifying a cultivated tomato plant, preferably a cultivated *Solanum lycopersicum* plant, producing fruits exhibiting an increased sucrose content and having at least one copy of a sucrose modifier SucMod allele and two copies of a sucrose accumulation TIV allele derived from a green-fruited wild tomato accession, comprising the steps of:
a) Detecting a nucleotide G at a position which corresponds to position 310 of SEQ ID NO: 1, and/or a nucleotide T at a position which corresponds to position 498 of SEQ ID NO: 1; and;
b) Detecting a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

In a further embodiment, the invention relates to the method of the preceding embodiment wherein step b) is carried out by further detecting a nucleotide C at a position which corresponds to position 1056 of SEQ ID NO: 6; and/or a nucleotide G at a position which corresponds to position 179 of SEQ ID NO: 6.

The use of the SucMod$^{chm}$ allele in an elite cultivar background and in combination with a wild allele of TIV such as a TIV$^{hab}$ allele as described herein has been shown to result in further enhanced sucrose content, increased total sugar content and a differential accumulation of fructose and glucose hexoses versus sucrose accumulation, which result in a unique and enhanced fruit flavour and taste perception. This invention therefore has the potential to be used in future breeding programs for improving tomato fruit flavour and taste.

BRIEF DESCRIPTION OF THE DRAWINGS

FIG. 4 shows sequence alignments and percent identity matrix of the SucMod/VIF allelic sequences of *Solanum lycopersicum* (Solyc12g099190), *Solanum chmielewskii* BD732 (SEQ ID NO: 1) and *Solanum pennellii* LA0716 (Solpen12g033870), and the homologous sequences from *Solanum cheesmaniae* LA0429, and *Solanum pimpinellifolium* LA1589.

FIG. 5: Sequence alignments and percent identity matrix of the TIV allelic sequences of *Solanum habrochaites* (SEQ ID NO: 6), *Solanum peruvianum* (KY565130), *Solanum pennellii* (XM015214462), *Solanum chmielewskii* (KY565126), *Solanum lycopersicum* (NM001247914), *Solanum lycopersicum* var *cerasiforme* (GU784870), *Solanum cheesmaniae* (KY565124) and *Solanum pimpinellifolium* (Z12026).

DETAILED DESCRIPTION OF THE INVENTION

Definitions

Figure 1:
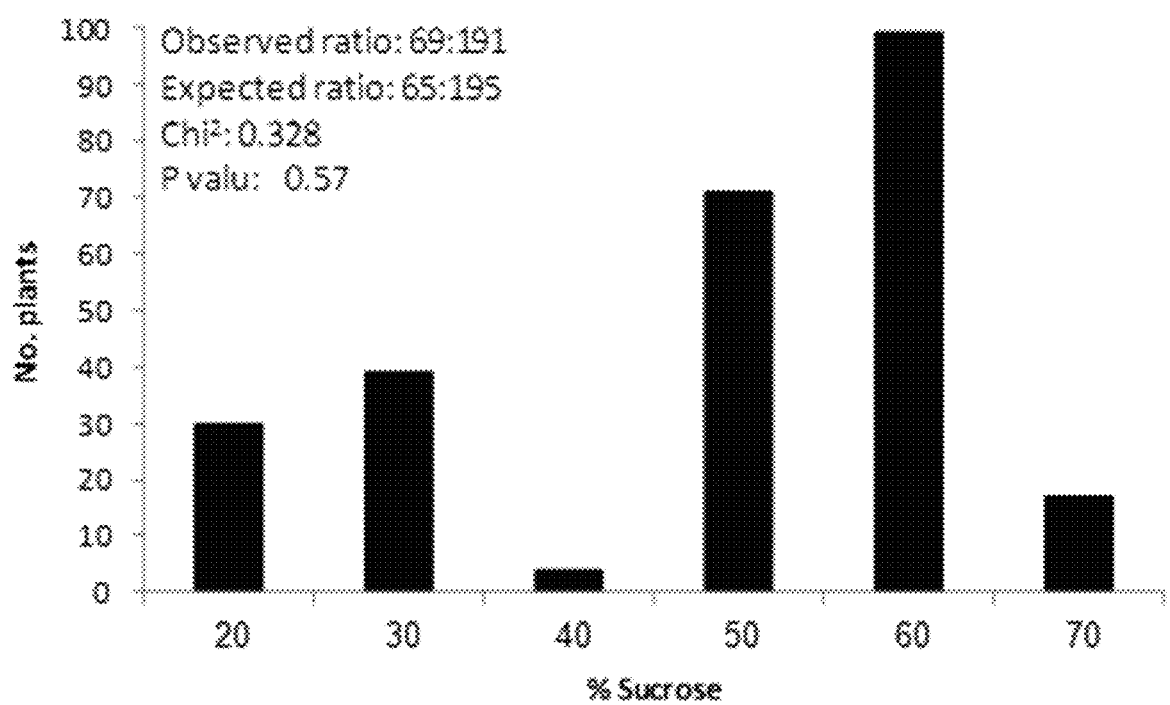
FIG. 1 shows a distribution of the fruit sucrose content (%) in mature tomato fruit from 15 combined F8 segregating population derived from the high sucrose content line 4510, showing bimodal distribution indicative of single monogenic inheritance.

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used herein, the term "about" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

A "cultivated tomato" plant is understood within the scope of the invention to refer to a plant that is no longer in the natural state but has been developed and domesticated by human care and for agricultural use and/or human consumption, and excludes wild tomato accessions, such as *Solanum chmielewskii* BD732 and *Solanum habrochaites* LA1777. As a matter of example, in embodiments, a tomato plant according to the present invention is capable of growing yellow, orange or red fruits. Alternatively or additionally, the cultivated tomato plant is a hybrid plant. Alternatively or additionally, the cultivated tomato plant is a *Solanum lycopersicum* plant. In the context of an interspecific cross between a *Solanum lycopersicum* plant and a wild tomato accession, a cultivated tomato plant is defined as a progeny plant of said interspecific cross, wherein said progeny plant has been backcrossed at least three times against a *Solanum lycopersicum* plant.

An "allele" is understood within the scope of the invention to refer to alternative or variant forms of various genetic units identical or associated with different forms of a gene or of any kind of identifiable genetic determinant, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a qualitative trait may comprise alternative or variant forms of various genetic units including those that are identical or associated with a single gene or multiple genes or their products or even a gene disrupting or controlled by a genetic determinant contributing to the phenotype represented by the locus.

Relatively speaking, the term "increased sucrose content" is herein understood to mean that a plant according to the present invention, e.g. comprising a) at least one copy of a sucrose modifier SucMod allele having at least 90% genetic similarity with SEQ ID NO: 1, and; b) two copies of a sucrose accumulation TIV allele derived from a green-fruited wild tomato accession, is capable of producing fruits exhibiting an increased sucrose content when compared with a plant lacking said alleles. In a preferred embodiment, the sucrose content is measured when the tomato fruits reach the red ripe stage.

"Increased sucrose content" is understood within the scope of the invention to mean tomato fruit which has a statistically significant increased sucrose content compared to fruit from a control plant (for example as described in the Example section), using standard error and/or at P<0.05 or P<0.01 using Student's test.

A "control tomato plant" is understood within the scope of the invention to mean a tomato plant that has the same genetic background as the cultivated tomato plant of the present invention wherein the control plant does not have any of the at least one alleles of the present invention linked to increased sucrose content. In particular a control tomato plant is a tomato plant belonging to the same plant variety and does not comprise any of the at least one alleles. The control tomato plant is grown for the same length of time and under the same conditions as the cultivated tomato plant of the present invention. Plant variety is herein understood according to definition of UPOV. Thus a control tomato plant may be a near-isogenic line, an inbred line or a hybrid provided that they have the same genetic background as the tomato plant of the present invention except the control plant does not have any of the at least one alleles of the present invention linked to increased sucrose content.

The term "trait" refers to a characteristic or a phenotype. In the context of the present invention, a sucrose content trait is an increased sucrose content trait. A trait may be inherited in a dominant or recessive manner, or in a partial or incomplete-dominant manner. A trait may be monogenic or polygenic, or may result from the interaction of one or more genes with the environment. A tomato plant can be homozygous or heterozygous for the trait.

The terms "hybrid", "hybrid plant", and "hybrid progeny" refer to an individual produced from genetically different parents (e.g. a genetically heterozygous or mostly heterozygous individual).

The term "inbred line" refers to a genetically homozygous or nearly homozygous population. An inbred line, for example, can be derived through several cycles of brother/sister breeding or of selfing or in dihaploid production.

The term "dihaploid line" refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially no longer segregating (stable).

The term "cultivar" or "variety" refers to a horticultural derived variety, as distinguished from a naturally occurring variety. In some embodiments of the present invention the cultivars or varieties are commercially valuable.

The term "genetically fixed" refers to a genetic element which has been stably incorporated into the genome of a plant that normally does not contain the genetic element. When genetically fixed, the genetic element can be transmitted in an easy and predictable manner to other plants by sexual crosses.

The term "plant" or "plant part" refers hereinafter to a plant part, organ or tissue obtainable from a tomato plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the sucrose content traits according to the invention, particularly when grown into a plant that produces fruits.

A "plant" is any plant at any stage of development.

A tomato plant seed is a seed which grows into a tomato plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Immature Green stage" is defined as when the fruits are unripe and still growing in size. This stage is understood to be the first stage in the ripening process.

"Mature green stage" is defined as when the fruit is fully expanded mature, but unripe and follows the "immature green stage" in the ripening process.

"Breaker stage" is defined as first sign of changing colour from green to pink colour in the external portion of the fruit.

"Red ripe stage" is defined as when the fruits are fully red, with no sign of green colour.

"Inner pericarp" and "outer pericarp" are understood within the scope of the invention to mean fruit tissue where the outer pericarp is the layer (approximately 2 mm) immediately below the outer epidermis and above the vascular tissue layer. The inner pericarp is from approximately 3 mm up to 10 mm below the vascular layer and before the inner epidermis.

"Processed food" is understood within the scope of the invention to mean food which has been altered from its natural state, e.g. tomato paste. Methods used for processing food include but are not limited to canning, freezing, refrigeration, dehydration and aseptic processing. The plants of the invention are particularly advantageous in processes using heating, which may cause a hydrolysis of the sucrose into hexose sugars, and therefore a decrease in sucrose content in fruits grown therefrom. However, since the fruits grown from the plants of the invention have an increased sucrose content, the loss in sucrose during processing will be less impactful for the resulting flavour and taste. Furthermore, the increase in total sugar content will be retained since the additional sucrose will have been broken into hexose moieties.

"Fresh cut market" is understood within the scope of the invention to mean vegetables on the market which have been minimally processed.

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes. In the context of the invention, a tomato plant comprising two identical copies of a particular allele at a particular locus, e.g. the SucMod$^{chm}$ allele at locus Solyc12g099190, is homozygous on a corresponding locus.

"Heterozygous" is understood within the scope of the invention to refer to unlike alleles at one or more corresponding loci on homologous chromosomes. In the context of the invention, a tomato plant comprising one copy of a particular allele at a particular locus, e.g. the SucMod$^{chm}$ allele at locus Solyc12g099190, is heterozygous on a corresponding locus.

A "dominant" allele is understood within the scope of the invention to refer to an allele which determines the phenotype when present in the heterozygous or homozygous state.

A "recessive" allele refers to an allele which determines the phenotype when present in the homozygous state only.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may comprise a gene or any other genetic determinant or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "genetic architecture at the quantitative trait locus" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A "genetic marker" can be physically located in a position on a chromosome that is within or outside the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (i.e., exhibits a normal distribution between two extremes).

A "quantitative trait" is typically the result of a genetic locus interacting with the environment or of multiple genetic loci interacting with each other and/or with the environment. Examples of quantitative traits include plant height and yield.

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

The term "recipient tomato plant" is used herein to indicate a tomato plant that is to receive DNA obtained from a donor tomato plant that comprises an allele for increased sucrose content. Said "recipient tomato plant" may or may not already comprise one or more alleles for sucrose content, in which case the term indicates a plant that is to receive an additional allele at a different locus.

The term "natural genetic background" is used herein to indicate the original genetic background of an allele. Such a background may for instance be the genome of a wild accession of tomato. For instance, the alleles of the present invention were found at specific locations on chromosome 3 and 12 of *Solanum habrochaites* and *Solanum chmielewskii*, respectively. As an example, *Solanum chmielewskii* represents the natural genetic background of the SucMod$^{chm}$ allele on chromosome 12 of *Solanum chmielewskii*. Conversely, a method that involves the transfer of DNA comprising this allele from chromosome 12 of *Solanum chmielewskii* to the same position on chromosome 12 of another tomato species, preferably a cultivated tomato plant, even more preferably a *Solanum lycopersicum* plant, will result in this allele not being in its natural genetic background.

A "donor tomato plant" is understood within the scope of the invention to mean the tomato plant which provides at least one allele linked to increased sucrose content.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower colour, and several known disease resistances such as, for example, Fungus spot resistance or Tomato Mosaic Virus resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (ie amplified sequence or target), one or more labeled allele-specific oligonucleotide probes and a detection system that records and interprets the hybridization signal.

The presence or absence of the desired allele may be determined by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Solanum* used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

In accordance with the present invention, the term "said position corresponding to position X", X being any number to be found in the respective context in the present application, does not only include the respective position in the SEQ ID NO referred to afterwards but also includes any sequence encoding a SucMod or a TIV allele, where, after alignment with the reference SEQ ID NO, the respective position might have a different number but corresponds to that indicated for the reference SEQ ID NO. Alignment of SucMod or TIV allele sequences can be effected by applying various alignment tools in a sensible manner, and for example by applying the tools described below.

"Genetic similarity or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, WI 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The "thermal melting point" is the temperature (under defined ionic strength and pH) at which 50% of the target sequence hybridizes to a perfectly matched probe. Very stringent conditions are selected to be equal to the melting temperature ($T_m$) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

Plants, Seeds, Fruits.

In a first embodiment, the invention provides a cultivated tomato plant, preferably a cultivated *Solanum lycopersicum* plant, comprising:
  a) at least one copy of a sucrose modifier SucMod allele having at least 90% genetic similarity with SEQ ID NO: 1, and;
  b) two copies of a sucrose accumulation TIV allele derived from a green-fruited wild tomato accession;
wherein said plant produces tomato fruit exhibiting an increased sucrose content compared with the same cultivated tomato plant lacking said SucMod and TIV alleles.

In a further embodiment, the SucMod allele comprises a nucleotide G at a position which corresponds to position 310 of SEQ ID NO: 1 and/or a nucleotide T at a position which corresponds to position 498 of SEQ ID NO: 1.

In a further embodiment, the invention provides a plant according to any of the preceding embodiments, wherein the sucrose content of tomato fruits reaching the red ripe stage is increased by 50%, more preferably by 75%, even more preferably by 100%, particularly by 200% when compared with the same cultivated tomato plant lacking said SucMod and TIV alleles.

In an alternative or additional embodiment, the plant of the invention is a plant according to any of the preceding embodiments, wherein said plant produces tomato fruits exhibiting a sucrose content of at least about 10 $mg.g^{-1}$ of fresh weight when reaching the red ripe stage. In a further embodiment, the plant of the invention produces tomato fruits exhibiting a sucrose content of at least about 12 $mg.g^{-1}$ of fresh weight when reaching the red ripe stage. In a further embodiment, the plant of the invention produces tomato fruits exhibiting a sucrose content of at least about 15 $mg.g^{-1}$ of fresh weight when reaching the red ripe stage. In a further embodiment, the plant of the invention produces tomato fruits exhibiting a sucrose content of at least about 20 $mg.g^{-1}$ of fresh weight when reaching the red ripe stage.

In an alternative or additional embodiment, the invention provides a cultivated tomato plant, preferably a cultivated *Solanum lycopersicum* plant, comprising:
  a) at least one copy of a sucrose modifier SucMod allele having at least 90% genetic similarity with SEQ ID NO: 1, and;
  b) two copies of a sucrose accumulation TIV allele derived from a green-fruited wild tomato accession;
wherein said SucMod allele comprises a nucleotide G at a position which corresponds to position 310 of SEQ ID NO: 1 and/or a nucleotide T at a position which corresponds to position 498 of SEQ ID NO: 1, and,
wherein said plant produces tomato fruit exhibiting an increased sucrose to hexose ratio when compared with the same cultivated tomato plant lacking said SucMod and TIV alleles.

In a further embodiment, the invention provides a plant according to any of the preceding embodiment, wherein the sucrose to hexose ratio of tomato fruits reaching the red ripe stage is increased by 50%, more preferably by 75%, even more preferably by 100%, particularly by 200% when compared with the same cultivated tomato plant lacking said SucMod and TIV alleles.

In an alternative or additional embodiment, the plant of the invention is a plant according to any of the preceding embodiments, wherein said plant produces tomato fruits exhibiting a sucrose to hexose ratio of at least about 0.5 when reaching the red ripe stage. In a further embodiment, the plant of the invention produces tomato fruits exhibiting a sucrose to hexose ratio of at least about 1 when reaching the red ripe stage. In a further embodiment, the plant of the invention produces tomato fruits exhibiting a sucrose to hexose ratio of at least about 1.5 when reaching the red ripe stage. In a further embodiment, the plant of the invention produces tomato fruits exhibiting a sucrose to hexose ratio of at least about 2 when reaching the red ripe stage. In a further embodiment, the plant of the invention produces tomato fruits exhibiting a sucrose to hexose ratio of at least about 3 when reaching the red ripe stage.

In a further embodiment, the invention provides plant according any of the preceding embodiments, wherein said SucMod allele is derived from *Solanum chmielewskii* or

*Solanum pimpinellifolium*. In a further embodiment, the invention provides a plant according any of the preceding embodiments, wherein said SucMod allele is derived from *Solanum chmielewskii*. In a further embodiment, the invention provides a plant according any of the preceding embodiments, wherein said SucMod allele is derived from *Solanum chmielewskii* accession BD732 or *Solanum pimpinellifolium* accession LA1589. In a further embodiment, the invention provides plant according any of the preceding embodiments, wherein said SucMod allele is derived from *Solanum chmielewskii* accession BD732.

In an alternative or additional embodiment, any SucMod or VIF allele derived from a wild tomato species can be successfully used in the context of the present invention, provided that the SucMod or VIF allele of said wild tomato species is more highly expressed than the TIV allele in said same wild tomato species.

In a further embodiment, the invention provides a plant according to any of the preceding embodiments, wherein said SucMod allele comprises a nucleotide G at a position which corresponds to position 310 of SEQ ID NO: 1, and wherein said nucleotide G at a position which corresponds to position 310 of SEQ ID NO: 1 can be detected in a PCR by amplification of a DNA fragment with the pair of oligonucleotide primers: forward primer of SEQ ID NO: 2 and reverse primer of SEQ ID NO: 3 and favourable allele probe of SEQ ID NO: 4.

In a further embodiment, the SucMod allele has at least 92% genetic similarity with SEQ ID NO: 1. In a further embodiment, the SucMod allele has at least 95% genetic similarity with SEQ ID NO: 1. In a further embodiment, the SucMod allele has at least 97% genetic similarity with SEQ ID NO: 1. In a further embodiment, the SucMod allele has at least 98% genetic similarity with SEQ ID NO: 1. In a further embodiment, the SucMod allele has at least 99% genetic similarity with SEQ ID NO: 1.

In a further embodiment, the invention provides a plant according to any of the preceding embodiments, wherein said SucMod allele comprises a nucleotide sequence of SEQ ID NO: 1. In a further embodiment, the invention provides a plant according to any of the preceding embodiments, wherein said plant comprises SEQ ID NO: 1.

In a further embodiment, the invention provides a plant according to any of the preceding embodiments, wherein said TIV allele is derived from a tomato accession pertaining to the Eriopersicum group.

In a further embodiment, the invention provides a plant according to any of the preceding embodiments, wherein said TIV allele has at least 98% genetic similarity with SEQ ID NO: 6. In a further embodiment, the invention provides a plant according to any of the preceding embodiments, wherein said TIV allele has at least 99% genetic similarity with SEQ ID NO: 6.

In a further embodiment, the invention provides a plant according to any of the preceding embodiments, wherein said TIV allele comprises a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6

In a further embodiment, the invention provides a plant according to any the preceding embodiments, wherein said TIV allele is derived from *Solanum habrochaites*. In a further embodiment, the invention provides a plant according to any the preceding embodiments, wherein said TIV allele is derived from *Solanum habrochaites* accession LA1777.

In a further embodiment, the invention provides a plant according to any of the preceding embodiments, wherein said TIV allele comprises a nucleotide C at a position which corresponds to position 1056 of SEQ ID NO: 6; and/or a nucleotide G at a position which corresponds to position 179 of SEQ ID NO: 6.

In an alternative or additional embodiment, any TIV allele derived from a wild tomato species can be successfully used in the context of the present invention, provided that the TIV allele of said wild tomato species is less expressed than the SucMod or VIF allele in said same wild tomato species.

In a further embodiment, the invention provides a plant according to any of the preceding embodiments, wherein said TIV allele has a nucleotide sequence of SEQ ID NO: 6. In a further embodiment, the invention provides a plant according to any of the preceding embodiments, wherein said plant comprises SEQ ID NO: 6.

In a further embodiment, the invention provides a cultivated tomato plant, preferably a cultivated *Solanum lycopersicum* plant, comprising:
 a) at least one copy of a sucrose modifier SucMod allele having at least 90% genetic similarity with SEQ ID NO: 1, and;
 b) two copies of a sucrose accumulation TIV allele derived from a green-fruited wild tomato accession;
wherein said SucMod allele is derived from a wild tomato species, wherein said SucMod allele is more highly expressed than the TIV allele in said same wild tomato species, and,
wherein said TIV allele derived from a green-fruited wild tomato accession is less expressed than the SucMod allele in said same wild tomato species, and, wherein said plant produces tomato fruit exhibiting an increased sucrose content compared with the same cultivated tomato plant lacking said SucMod and TIV alleles.

In a further embodiment, the invention provides a cultivated *Solanum lycopersicum* plant comprising at least one copy of SucMod allele from *Solanum chmielewskii* and two copies of a TIV allele from *Solanum habrochaites*, wherein said plant produces tomato fruit exhibiting an increased sucrose content compared with the same cultivated tomato plant lacking said SucMod and TIV alleles.

In a further embodiment, the invention provides a plant according to any of the preceding embodiments, wherein said plant comprises two copies of the SucMod allele. In a further embodiment, the invention provides a plant according to any of the preceding embodiments, wherein said plant is homozygous for the SucMod allele. In a further embodiment, the invention provides a plant according to any the preceding embodiments, wherein said plant is homozygous for the SucMod$^{chm}$ allele. In a further embodiment, the invention provides a plant according to any of the preceding embodiments, wherein said plant is homozygous for the SucMod$^{chm}$ allele of SEQ ID NO: 1.

In a further embodiment, the invention provides a plant according to any of the preceding embodiments, wherein said TIV allele and said SucMod allele are obtainable, obtained or derived from *Solanum lycopersicum* line TIPC18-61141, deposited with NCIMB on 20 Aug. 2018 under NCIMB Accession No. 43169. In a further embodiment, the invention provides a plant according to any of the preceding embodiments, wherein said plant is obtained by crossing *Solanum lycopersicum* line TIPC18-61141, deposited with NCIMB on 20 Aug. 2018 under NCIMB Accession No. 43169, or a progeny or an ancestor thereof, with a tomato plant lacking said SucMod and TIV alleles. In a further embodiment, the invention provides a plant according to any of the preceding embodiments, wherein *Solanum lycopersicum* line TIPC18-61141, deposited with NCIMB on 20 Aug. 2018 under NCIMB Accession No. 43169, or a progeny or an ancestor thereof, is the source of the SucMod and TIV alleles of the invention. In a further embodiment, the invention provides a plant according to any of the preceding embodiments, wherein said SucMod and TIV alleles of the invention are introgressed from *Solanum lycopersicum* line TIPC18-61141, deposited with NCIMB on 20 Aug. 2018 under NCIMB Accession No. 43169, or a progeny or an ancestor thereof.

In a further embodiment, the invention provides a plant according to any of the preceding embodiments, wherein said plant is a haploid, a dihaploid, an inbred or a hybrid cultivated tomato plant.

In another embodiment, the plant according to the invention is male sterile. In another embodiment, the plant according to the invention is cytoplasmic male sterile.

In another embodiment, the plant according to the invention grows mature tomato fruits, wherein the fruit colour is yellow, red or orange.

It is a further embodiment to provide a plant part, organ or tissue obtainable from a cultivated tomato plant, preferably a cultivated *Solanum lycopersicum* according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the increased sucrose content trait according to the invention, particularly when grown into a plant that produces fruits.

In a further embodiment, the invention provides tomato fruit produced by a tomato plant according to any of the preceding embodiments.

In a further embodiment, the invention provides a tomato seed that produces a tomato plant according to any of the preceding embodiments.

Alleles, Markers.

The present invention is further directed to SucMod and TIV alleles directing or controlling expression of the sucrose content trait in the tomato plant. In a further embodiment, the alleles of the present invention are located on chromosome 3 and 12, respectively. In a further embodiment of the present invention, the SucMod and TIV alleles of the invention are obtainable, obtained or derived from a donor plant which has the genetic background of *Solanum lycopersicum* line TIPC18-61141, deposited with NCIMB on 20 Aug. 2018 under NCIMB Accession No. 43169, or a progeny or an ancestor thereof, and comprising said SucMod and TIV alleles of the invention.

In a further embodiment, the invention relates to an isolated nucleotide sequence comprising SEQ ID NO: 1.

In a further embodiment, the alleles of the present invention are genetically or physically linked to 3 marker loci, which co-segregate with the sucrose content trait and are marker locus ST3226 for the SucMod alleles; and marker loci ST3472 and ST3478 for the TIV$^{hab}$ allele, or any adjacent marker that is statistically correlated and thus co-segregates with the sucrose content trait.

In another embodiment, said SucMod and TIV alleles of the invention, or functional parts thereof, are genetically linked to 3 marker loci respectively, wherein:
  i. marker locus ST3226 can be identified in a PCR by amplification of a DNA fragment with the pair of oligonucleotide primers: forward primer of SEQ ID NO: 2 and reverse primer of SEQ ID NO: 3 and favourable allele probe of SEQ ID NO: 4,
  ii. marker locus ST3472 can be identified in a PCR by amplification of a DNA fragment with the pair of oligonucleotide primers: forward primer of SEQ ID NO: 7 and reverse primer of SEQ ID NO: 8 and favourable allele probe of SEQ ID NO: 9,
  iii. marker locus ST3478 can be identified in a PCR by amplification of a DNA fragment with the pair of oligonucleotide primers: forward primer of SEQ ID NO: 11 and reverse primer of SEQ ID NO: 12 and favourable allele probe of SEQ ID NO 13.

The present invention discloses a kit for the detection of the sucrose content trait locus in a cultivated tomato plant, particularly a cultivated *Solanum lycopersicum* plant, wherein said kit comprises at least one PCR oligonucleotide primer pair and probe, selected from:
  a. primer pair represented by a forward primer of SEQ ID NO: 2 and a reverse primer of SEQ ID NO: 3 and probes of SEQ ID NO: 4 and 5 or;
  b. primer pair represented by a forward primer of SEQ ID NO: 7 and a reverse primer of SEQ ID NO: 8 and probes of SEQ ID NO: 9 and 10 or;
  c. primer pair represented by a forward primer of SEQ ID NO: 11 and a reverse primer of SEQ ID NO: 12 and probes of SEQ ID NO: 13 and 14 or;
another primer or primer pair representing an adjacent marker that is statistically correlated and thus co-segregates with the sucrose content trait.

In addition to SNP marker ST3226, another SNP marker associated with the SucModIVIF alleles of the invention, at least with the VIF$^{pimp}$ allele of the invention, is disclosed in Example 7 and FIG. 4.

Furthermore, in addition to the two SNP markers ST3272 and ST3274 associated with the TIV$^{hab}$ allele of the invention, 8 SNP markers associated with additional TIV alleles of the invention are disclosed in Example 8 and FIG. 5.

The skilled person in the art is able to design corresponding primers and probes at its convenience and without any burden, based on the sequence information disclosed herein.

The present invention also discloses the use of some or all of these SNP markers according to the invention for diagnostic selection and/or genotyping of the sucrose content trait locus in a cultivated tomato plant, particularly a cultivated *Solanum lycopersicum* plant.

The present invention further discloses the use of some or all of these SNP markers for identifying in a tomato plant, particularly a cultivated tomato plant, more particularly a *Solanum lycopersicum* plant according to the invention, the presence of sucrose content trait locus and/or for monitoring the introgression of the sucrose content trait locus in a cultivated tomato plant, particularly a *Solanum lycopersicum* plant according to the invention and as described herein.

The invention further discloses a polynucleotide (amplification product) obtainable in a PCR reaction involving at least one oligonucleotide primer or a pair of PCR oligonucleotide primers selected from the group consisting of SEQ ID NO 2 and SEQ ID NO 3; SEQ ID NO 7 and SEQ ID NO 8; SEQ ID NO 11 and SEQ ID NO 12; and reacting with favourable allele probes selected from the group comprising SEQ ID NO 4, SEQ ID NO 9 or SEQ ID NO 13 or by another primer representing an adjacent marker that is statistically correlated and thus co-segregates with the sucrose content trait or with one of the markers disclosed, which amplification product corresponds to an amplification product obtainable from *Solanum lycopersicum* line TIPC18-61141, deposited with NCIMB on 20 Aug. 2018 under NCIMB Accession No. 43169, or a progeny or an ancestor thereof, comprising the SucMod and TIV alleles of the invention, in a PCR reaction with identical primers or primer pairs provided that the respective marker locus is still present in said tomato plant and/or can be considered an allele thereof.

Also contemplated herein is a polynucleotide that has at least 90%, particularly at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the sucrose content trait locus.

The present invention therefore further relates in one embodiment to derived markers, particularly to derived primers or probes, developed from an amplification product according to the invention and as described herein above by methods known in the art, which derived markers are genetically linked to the sucrose content trait locus.

Methods of Breeding.

In another embodiment the invention relates to a method of providing a cultivated tomato plant, preferably a cultivated plant *Solanum lycopersicum*, plant part or seed, wherein said method comprises the following steps:
  a) Crossing a $1^{st}$ plant according with any of the preceding embodiments with a 2 nd tomato plant lacking the SucMod and TIV alleles of the invention,
  b) Obtaining a progeny tomato plant, and,
  c) Optionally, selecting a plant of said progeny characterized in that said plant produces fruits exhibiting an increased sucrose content.

In a further embodiment, the invention provides a method for producing a cultivated tomato plant, preferably a cultivated *Solanum lycopersicum* plant, producing tomato fruits exhibiting increased sucrose content comprising the steps of
  a) crossing a $1^{st}$ plant according to any of the preceding embodiments comprising at least one copy of a sucrose modifier SucMod allele and two copies of a sucrose accumulation TIV allele with a $2^{nd}$ cultivated tomato plant lacking said SucMod and TIV alleles;
  b) Selecting a progeny plant producing fruits exhibiting an increased sucrose content;
wherein the selection of step b) is carried out by detecting a nucleotide G at a position which corresponds to position 310 of SEQ ID NO: 1, and/or, by detecting a nucleotide T at a position which corresponds to position 498 of SEQ ID NO: 1; and, by detecting a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

In a further embodiment, the invention relates to the method of any the preceding embodiments wherein the selection of step b) is carried out by further detecting a nucleotide C at a position which corresponds to position 1056 of SEQ ID NO: 6; and/or a nucleotide G at a position which corresponds to position 179 of SEQ ID NO: 6.

In a further embodiment the invention relates to the method of any of the preceding embodiments wherein the $1^{st}$ plant of step a) is *Solanum lycopersicum* line TIPC18-61141, deposited with NCIMB on 20 Aug. 2018 under NCIMB Accession No. 43169.

In another embodiment, the invention relates to the method of any of the preceding embodiments, wherein said progeny plant exhibiting a sucrose content of at least about 10, preferably 12, more preferably 15, even more preferably 15 $mg.g^{-1}$ of fresh weight when reaching the red ripe stage.

In a further embodiment, the invention provides a method for producing a cultivated tomato plant, preferably a cultivated *Solanum lycopersicum* plant, producing tomato fruits exhibiting increased sucrose to hexose ratio comprising the steps of
  a) crossing a $1^{st}$ plant according to any of the preceding embodiments comprising at least one copy of a sucrose modifier SucMod allele and two copies of a sucrose accumulation TIV allele with a $2^{nd}$ cultivated tomato plant lacking said SucMod and TIV alleles;
  b) Selecting a progeny plant producing fruits exhibiting an increased sucrose content;
wherein the selection of step b) is carried out by detecting a nucleotide G at a position which corresponds to position 310 of SEQ ID NO: 1, and/or, by detecting a nucleotide T at a position which corresponds to position 498 of SEQ ID NO: 1, and, by detecting a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

In a further embodiment, the invention relates to the method of any of the preceding embodiments wherein the selection of step b) is carried out by further detecting a nucleotide C at a position which corresponds to position 1056 of SEQ ID NO: 6; and/or a nucleotide G at a position which corresponds to position 179 of SEQ ID NO: 6.

In another embodiment, the invention relates to the method of preceding embodiment, wherein said plant of step c) produces tomato fruits exhibiting a sucrose to hexose ratio of at least about 0.5, preferably at least about 1, preferably at least about 1.2, more preferably at least about 1.5, even more preferably at least 2.0 when reaching the red ripe stage.

In another embodiment the invention relates to a method of providing a cultivated tomato plant, preferably a cultivated *Solanum lycopersicum* plant, producing tomato fruits exhibiting increased sucrose content comprising the steps of:

a) Crossing a 1st plant according with any of the preceding embodiments with a 2 nd tomato plant lacking the SucMod and TIV alleles of the invention,
b) Obtaining a progeny cultivated tomato plant, and,
c) Optionally, selecting a plant of said progeny characterized in that said plant produces fruits exhibiting a sucrose content increased by 50%, more preferably by 75%, even more preferably by 100%, particularly by 200% when compared with the same cultivated tomato plant lacking said SucMod and TIV alleles.

In a further embodiment is considered the method of any of the preceding embodiments wherein the 1st tomato plant of step a) is *Solanum lycopersicum* line TIPC18-61141, deposited with NCIMB on 20 Aug. 2018 under NCIMB Accession No. 43169, or a progeny or an ancestor thereof.

In another embodiment is considered a method for producing a cultivated tomato plant, preferably a cultivated *Solanum lycopersicum* plant, producing tomato fruits exhibiting increased sucrose content comprising the following steps:
  a) Providing seeds of a tomato plant according to any of the previous embodiments,
  b) Germinating said seed and growing a mature, fertile plant therefrom,
  c) Inducing self-pollination of said plant under a), growing fruits and harvesting the fertile seeds therefrom, and
  d) Growing plants from the seeds harvested under c) and selecting an increased sucrose content plant.

In a further embodiment, the invention relates to a method for producing a cultivated tomato plant, preferably a cultivated *Solanum lycopersicum* plant, producing tomato fruits exhibiting increased sucrose content comprising the steps of:
  a. selecting a tomato plant, which comprises 3 marker loci, which co-segregate with the sucrose content trait and are marker locus ST3226 for the SucMod alleles; and marker loci ST3472 and ST3478 for the TIV$^{hab}$ allele, or any adjacent marker that is statistically correlated and thus co-segregates with the sucrose content trait,
  b. crossing said plant of step a), with a cultivated tomato plant, preferably a cultivated *Solanum lycopersicum* plant, which does not comprise said SucMod and TIV alleles, and
  c. selecting progeny tomato plant from said cross which comprises a sucrose content trait and demonstrates association with said 3 marker loci of step a) and produces tomato fruits exhibiting increased sucrose content.

It is a further embodiment of the present invention to provide a method for increasing the sucrose content of fruits produced by a tomato plant, comprising the steps of:
  a) selecting a tomato plant, which comprises 3 marker loci, which co-segregate with the sucrose content trait and are marker locus ST3226 for the SucMod alleles; and marker loci ST3472 and ST3478 for the TIV$^{hab}$ allele, or any adjacent marker that is statistically correlated and thus co-segregates with the sucrose content trait,
  b) crossing said tomato plant of step a), which comprises a sucrose content trait, with a recipient cultivated tomato plant, which does not comprise a sucrose content trait, and
  c) selecting progeny from said cross which shows increased sucrose content, as compared to the recipient plant of step b), and demonstrates association of the increased sucrose content with 3 marker loci ST3226, ST3472 and ST3478 of step a).

It is a further embodiment of the present invention to provide a method for providing tomato plants producing fruits exhibiting an increase sucrose content by introducing into a tomato plant a nucleotide sequence of SEQ ID NO: 1. In a further embodiment, the method of the preceding embodiment wherein the nucleotide sequence of SEQ ID NO: 6 is additionally introduced into said tomato plant.

The sucrose content alleles can also be introduced by way of mutagenesis, for example by way a chemical mutagenesis, for example by way of EMS mutagenesis. Alternatively, the sucrose content alleles can also be identified and/or introduced by way of using TILLING techniques.

The sucrose content alleles can also be introduced by targeted mutagenesis, e.g. by way of homologous recombination, zinc-finger nucleases, oligonucleotide-based mutation induction, transcription activator-like effector nucleases (TALENs), clustered regularly interspaced short palindromic repeat (CRISPR) systems or any alternative technique to edit the genome.

Alternatively, the sucrose content alleles can also be introduced by transgenic or cis-genic methods via a nucleotide construct which may be comprised in a vector.

Methods of Selection.

In a further embodiment, the invention provides a method for identifying a cultivated tomato plant, preferably a cultivated *Solanum lycopersicum* plant, producing fruits exhibiting an increased sucrose content and having at least one copy of a sucrose modifier SucMod allele and two copies of a sucrose accumulation TIV allele derived from a green-fruited wild tomato accession, comprising the steps of:
  a) Detecting a nucleotide G at a position which corresponds to position 310 of SEQ ID NO: 1, and/or a nucleotide T at a position which corresponds to position 498 of SEQ ID NO: 1; and,
  b) Detecting a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

In a further embodiment, the invention relates to the method of the preceding embodiment wherein step b) is carried out by further detecting a nucleotide C at a position which corresponds to position 1056 of SEQ ID NO: 6; and/or a nucleotide G at a position which corresponds to position 179 of SEQ ID NO: 6.

The present invention further discloses methods of identifying a cultivated tomato plant, preferably a cultivated *Solanum lycopersicum* plant comprising a sucrose content trait, comprising the steps of:
  a) providing a population segregating for sucrose content,
  b) screening the segregating population for a member comprising a sucrose content trait, wherein said trait can be identified by the presence of 3 marker loci ST3226, ST3472 and ST3478,
  c) selecting one member of the segregating population, wherein said member comprises a sucrose content trait.

The present invention further discloses methods of identifying a cultivated tomato plant, preferably a cultivated *Solanum lycopersicum* plant, producing fruits exhibiting an increased sucrose content and having at least one copy of a sucrose modifier SucMod allele and two copies of a sucrose accumulation TIV allele derived from a green-fruited wild tomato accession, comprising the steps of:
  a) providing a population segregating for sucrose content,
  b) screening the segregating population for a member comprising a sucrose content trait, wherein said trait can be identified by the presence of 3 marker loci, which marker loci are on chromosome 3 and 12 respectively and co-segregate with the sucrose content trait and can be identified by a PCR oligonucleotide primer or a pair of PCR oligonucleotide primers selected from the group of primer pair represented by a forward primer of SEQ ID NO: 2 and a reverse primer of SEQ ID NO: 3, identifying marker locus ST3226; primer pair represented by a forward primer of SEQ ID NO: 7 and a reverse primer of SEQ ID NO: 8, identifying marker locus ST3472; and a primer pair represented by a forward primer of SEQ ID NO: 11 and a reverse primer of SEQ ID NO: 12, identifying marker locus ST3478,
  c) selecting one member of the segregating population, wherein said member comprises a sucrose content trait.

The present invention further discloses a method for detecting in a tomato plant a genotype linked with an increase sucrose content phenotype, comprising the steps of:
  a) Detecting by genotyping in a tomato plant a set of molecular markers comprising marker loci ST3226, ST3472 and ST3478 linked to an increased sucrose content;
  b) selecting said detected tomato plant comprising a set of molecular markers comprising marker loci ST3226, ST3472 and ST3478 linked to an increased sucrose content; and,
  c) crossing said selected tomato plant to produce progeny tomato plant comprising a set of molecular markers comprising marker loci ST3226, ST3472 and ST3478 linked to an increased sucrose content.

The method of any of the preceding embodiments, wherein said set of molecular markers can be detected by using SEQ ID NO: 1 to 14.

The method of any of the preceding embodiments, wherein the detected marker loci comprises a genotype having one allele of the G allelic state at marker locus ST3226, one allele of the C allelic state at marker locus ST3472 and one allele of the G allelic state at marker locus ST3478.

Uses.

In another embodiment the invention relates to the use of a cultivated tomato plant, preferably a cultivated *Solanum lycopersicum* plant, plant part or seed according to any of the preceding embodiments for producing and harvesting tomato fruits.

In another embodiment the invention relates to the use of a cultivated tomato plant, preferably a cultivated *Solanum lycopersicum* plant, according to any of the preceding embodiments for producing tomato fruits exhibiting an increased sucrose content for the fresh market or for food processing. It is of particular interest that the increased sucrose content is retained, even after food processing, such as canning or freezing. In a further embodiment, the invention provides processed food made from a tomato fruit produced by a cultivated tomato plant, preferably a cultivated *Solanum lycopersicum* plant, according to any of the preceding embodiments.

In another embodiment the invention relates to the use of a cultivated tomato plant, preferably a cultivated *Solanum lycopersicum* plant, plant part or seed according to any of preceding embodiments, wherein the cultivated tomato plant, preferably the cultivated *Solanum lycopersicum* plant, plant part or seed is *Solanum lycopersicum* line TIPC18-61141, deposited with NCIMB on 20 Aug. 2018 under NCIMB Accession No. 43169, or a progeny or an ancestor thereof.

In a further embodiment the invention relates to the use of a cultivated tomato plant, preferably a cultivated *Solanum lycopersicum* plant, plant part or seed according to any of the preceding embodiments to sow a field, a greenhouse, or a plastic house.

The present invention also relates to the use of sucrose content-propagating material obtainable from a tomato plant according to any of the preceding embodiments for growing a tomato plant in order to produce tomato plants producing tomato fruits exhibiting increased sucrose content, wherein said increased sucrose content may be assessed in a standard assay, particularly an assay as described in Example 9 below.

The present invention also provides a method of producing tomato fruits, the method comprising planting a seed according to any of the preceding embodiments, cultivating the tomato plant produced therefrom, and harvesting a tomato fruit produced by said tomato plant.

In a further embodiment the invention relates to the use of the alleles which are genetically or physically linked to 3 marker loci which co-segregate with the sucrose content trait and are marker loci ST3226, ST3472 and ST3478, respectively to confer the increased sucrose content trait to a tomato plant lacking said alleles.

The invention further relates to the use of a tomato plant according to any of the preceding embodiments to introgress a sucrose content trait into a tomato plant lacking said sucrose content trait.

The invention further relates to the use of SEQ ID NOs: 1 to 14 for marker assisted selection of plants. The invention further relates to the use of SEQ ID NOs: 1 to 14 for introgression into plants.

Based on the description of the present invention, the skilled person who is in possession of *Solanum lycopersicum* line TIPC18-61141, deposited with NCIMB on 20 Aug. 2018 under NCIMB Accession No. 43169, or a progeny or an ancestor thereof, comprising the SucMod and TIV alleles of the invention, as described herein, has no difficulty to transfer said alleles of the present invention to other tomato plants of various types using breeding techniques well-known in the art with the support of marker loci herein disclosed.

Seed Deposit Details

Applicant has made a deposit of 2500 seeds of *Solanum lycopersicum* line TIPC18-61141 with NCIMB on 20 Aug. 2018 under NCIMB Accession No. 43169.

Applicant elects for the expert solution and requests that the deposited material be released only to an Expert according to Rule 32(1) EPC or corresponding laws and rules of other countries or treaties (Expert Witness clause), until the mention of the grant of the patent publishes, or from 20 years from the date of filing if the application is refused, withdrawn or deemed to be withdrawn.

EXAMPLES

Example 1: Identification of a Novel Allele Associated with Increased Sucrose Content It was observed in Solanum lycopersicum line 2927 harbouring a Solanum habrochaites TIV (TIV$^{hab}$) introgression on chromosome 3 (derived from Solanum habrochaites LA1777) that sucrose accumulated to levels in the range of circa 10-20% of the total sugars (referred to as moderate sucrose accumulation) rather than the higher levels of 60-80% (high sucrose accumulation) found in the corresponding wild species itself (Table 1, rows in bold).

TABLE 1

Sugar levels in red ripe fruits of selected tomato wild accessions and near-isogenic Solanum lycopersicum lines homozygous for TIV$^{hab}$ or TIV$^{lyc}$ alleles. Data are the averages and SE of a minimum of 6 fruits from 3 plants.

| genotype | sucrose | glucose | fructose | total | % sucrose |
|---|---|---|---|---|---|
| S. habrochaites LA1777 | 13.3 ± 1.1 | 1.6 ± 0.3 | 3.63 ± 0.5 | 18.6 ± 1 | 71.7 ± 6.9 |
| S. habrochaites LA0407 | 26.1 ± 0.6 | 1.4 ± 0.3 | 5.8 ± 0.1 | 33.2 ± 1 | 78.4 ± 1.3 |
| S. chmiliewskii LA1318 | 33.9 ± 2.1 | 1.9 ± 0.5 | 4 ± 0.1 | 39.9 ± 1.5 | 84.9 ± 3.7 |
| S. chmiliewskii LA1028 | 20.5 ± 1.1 | 1 ± 0.2 | 3.1 ± 0.1 | 24.6 ± 0.8 | 83.2 ± 3.1 |
| Line 2927 BC3F9 TIV$^{hab/hab}$ | 3.9 ± 0.4 | 13.4 ± 0.5 | 14.2 ± 0.6 | 31.6 ± 1.3 | 12 ± 0.8 |
| Line 2927 BC3F9 TIV$^{lyc/lyc}$ | 0 | 13 ± 0.4 | 12.7 ± 0.4 | 25.7 ± 0.7 | 0 |

In order to study this phenomenon, segregating populations were developed based on the cross of a TIV$^{hab/hab}$ tomato introgression line (line 2927) with an introgression line harbouring the TIV allele from wild species Solanum chmielewskii BD732, which also accumulates high levels of sucrose (line 2928). In order to rule out possible effects of the two TIV alleles, TIV$^{hab}$ and TIV$^{chm}$, backcross populations were developed and selected through genotyping for the homozygous TIV$^{hab/hab}$ genotype background and high sucrose accumulation.

Results from 260 plants derived from segregating heterozygous F$_9$ populations (identified as 4510 and 4511) indicated that a single gene determines moderate versus high sucrose accumulation in the presence of the TIV$^{hab/hab}$ genotype and that high sucrose accumulation appears to be a dominant trait (FIG. 1).

Example 2: Identification of the Gene Underlying the High Sucrose Accumulation Trait In order to identify the gene responsible for the trait of high sucrose accumulation, which was named modifier of sucrose (SucMod), a QTL mapping was performed, followed by fine mapping at the level of the individual gene.

As a first step, the segregating F$_9$ populations of 260 plants described in Example 1 were screened for sucrose accumulation and 20 plants of F$_{10}$ populations derived from each of 20 moderate F$_9$ sucrose accumulators (presumably homozygous for the recessive Solanum lycopersicum moderate sucrose accumulation allele) and 20 plants of F$_{10}$ populations derived from each of 20 high F$_9$ sucrose accumulators (both heterozygous and homozygous for the dominant Solanum chmielewskii high sucrose accumulation allele) were selected. Based on the homozygosity test and according to segregation for sucrose levels amongst the 20 plants of each family, 15 homozygous moderate sucrose F10 families and 15 homozygous high sucrose F10 families were analysed by bulked segregant analysis, divided into 3 groups each of 5 F10 families and these were genotyped using the Illumina system. The trait was definitively localized to the distal region of chromosome 12, from SL2.40ch12:64,339, 465 to the distal end (based on Heinz v.6 genetic map), a region of nearly 1 Mb.

Interestingly, this region harbours three tandem genes encoding invertase inhibitors in the kb region from SL2.40ch12:64,769,000 to SL2.40ch12:64, 779,000. However, the complete ~1 Mbp region contains additional candidate genes as well, including sugar transporters, transcription factors and genes of unknown function. Therefore a fine mapping strategy was performed and 10,000 F10 plants derived from the heterozygous F9 plants were genotyped using the Illumina platform with markers at 4 positions along the region of interest and a total of 327 homozygous recombinants were selected and grown to produce ripe fruits for sugar analysis. The results of the sugar analysis on mature fruit of these recombinants allowed to limit the introgression of interest to a 440 kb region between SL2.40ch12:64,479,000 to SL2.40ch12:64,919,000. Forty six informative recombinants, representing both high and moderate accumulators were used for a stepwise fine mapping based on PCR cloning and sequencing of eight additional regions. Amongst the recombinants, two were informative in limiting the region on both sides to a single gene Solyc12g099190 and eliminating the two additional downstream invertase inhibitor genes as candidates for the QTL SucMod. Recombinant SM335 had a sucrose level of 55% and its recombination event was at the region upstream of the promoter region of the Solyc12g099190 locus, encoding a vacuolar invertase inhibitor (VIF). Recombinant SM79 had a sucrose level of 22% and its recombination event was at the region downstream of the 3' region of the gene.

In order to determine whether differences in gene transcription could account for the differential effect of the SucMod/VIF alleles, a RNA-seq analysis was carried out based on developing tomato fruits of near-isogenic TIV$^{hab/hab}$ lines of tomato differing in the VIF introgression, thus harbouring either SucMod$^{chm}$ or VIF$^{lyc}$ alleles. The results for the differential expression of the genes in the region clearly show a very large upregulation of SucMod$^{chm}$ compared to VIF$^{lyc}$ throughout fruit development (Table 2). TIV$^{hab}$ allele expression was not affected by the identity of the SucMod/VIF alleles.

TABLE 2

RPKM of SucMod/VIF alleles expression at three stages of fruit development. Results are averages of three individual RNA-seq libraries each developed from a minimum of four fruits from individual plants. Numbers represent averages and (s.e). The last row indicates the X fold increase in expression due to genotype when comparing the SucMod$^{chm}$ and VIF$^{lyc}$ alleles.

| genotype | Mature Green | Breaker | Red ripe |
|---|---|---|---|
| SucMod$^{chm}$ | 62 (+/−29) | 352 (+/−105) | 487 (+/−103) |
| VIF$^{lyc}$ | 13 (+/−6) | 12 (+/−2) | 21 (+/−2) |
| | X 4.6 | X 30.4 | X 23.5 |

Example 3: Effect of the SucMod/VIF Alleles on Sucrose and Sugar Contents

Figure 2A:
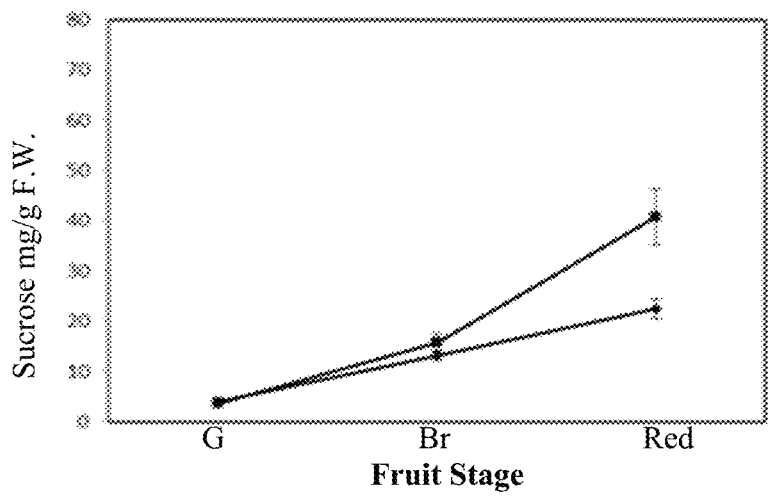
FIG. 2A, FIG. 2B, and FIG. 2C show sucrose, hexose and total sugar (sucrose+hexose) accumulation in developing fruit (G, mature green; BR, breaker; R, red ripe) of SucMod$^{chm/chm}$ (squares) and VIF$^{lyc/lyc}$ (diamonds) tomato lines in the TIV$^{hab/hab}$ background.
Figure 2B:
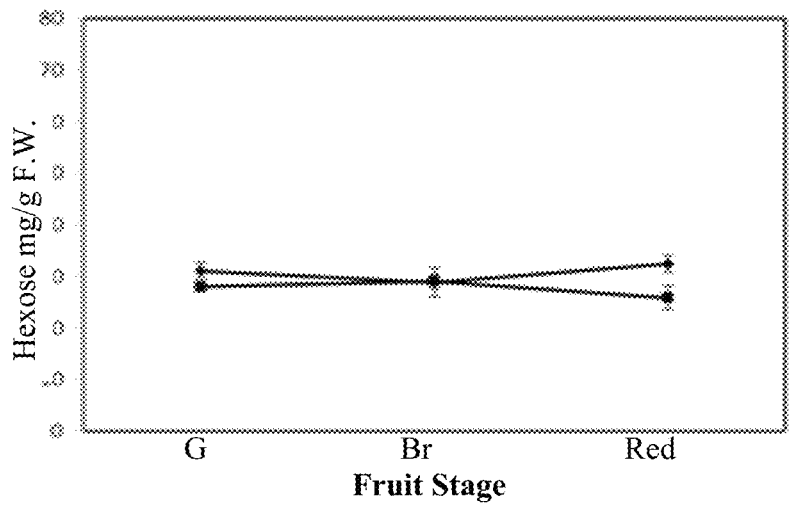
Figure 2C:
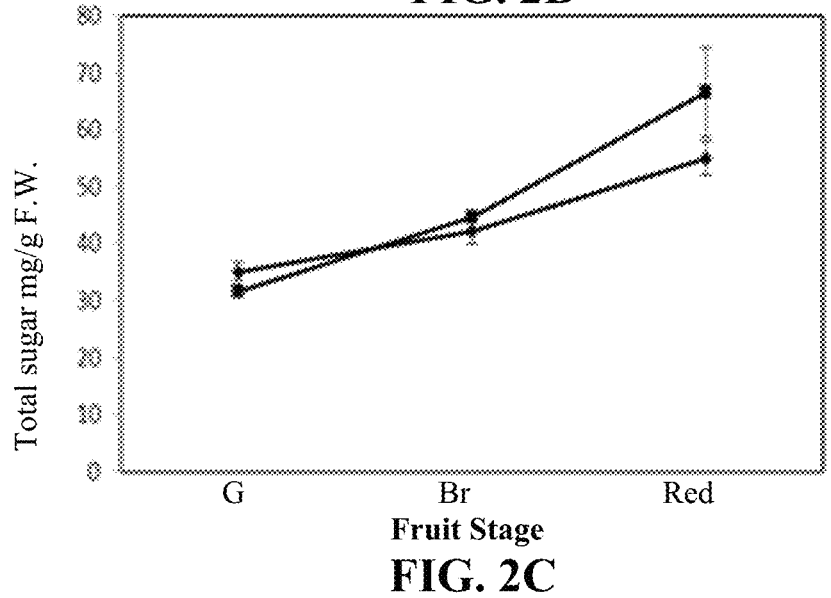

In order to determine the developmental stage during which the difference in sucrose accumulation can be observed due to the SucMod/VIF alleles, sugar levels were measured during development of a near-isogenic F14 line (based on the original cross between lines 2928 and 2927) segregating for the moderate (TIV$^{hab/hab}$ VIP$^{lyc/lyc}$) and high (TIV$^{hab/hab}$ SucMod$^{chm/chm}$) sucrose accumulation alleles. Developmentally, sucrose accumulation in both the moderate and high sucrose accumulation lines begins prior to the breaker stage but the rate of sucrose accumulation is significantly higher in the SucMod$^{chm/chm}$ genotype than in the VIF$^{lyc/lyc}$ genotype (FIG. 2A-C). Already at the breaker stage small but significant differences in sucrose levels due to the VIF genotype can be seen, and these differences increase with ripening (FIG. 2B).

The increase in sucrose levels is combined with an increase in total sugar content as well (FIG. 2A). In absolute values, there was a net increase in sucrose levels of 18 mg.g$^{-1}$ of fresh weight whereas the total sugars were increased by 13 mg.g$^{-1}$ of fresh weight. Thus, about 60% of the net sucrose increase is translated into net total sugar increase, due to the fact that hexose levels of the moderate accumulators is higher and accounts for a larger proportion of the total sugar content (FIG. 2C). Nevertheless, the high sucrose phenotype is accompanied by a net increase in total sugars.

In order to substantiate this observation, backcross populations harbouring two copies of the TIV$^{hab}$ allele and segregating for SucMod$^{chm}$ and VIF$^{lyc}$ alleles were developed. Soluble sugars and Brix were measured in red ripe fruits, and the results are presented in Table 3. It can be seen that total sugar content increases in parallel with increasing sucrose levels. Furthermore, the highest total sugar accumulators are also the highest sucrose accumulators. Finally, lines harbouring at least one copy of the SucMod$^{chm}$ allele exhibit a much higher sucrose to hexose ratio.

The results also show that the SucMod$^{chm}$ allele is completely dominant and that the heterozygous SucMod$^{chm}$/VIF$^{lyc}$ and homozygous SucMod$^{chm/chm}$ were indistinguishable in terms of the sucrose and hexose levels.

TABLE 3

Sugar levels of mature fruits in a segregating population for the SucMod$^{chm}$ and VIF$^{lyc}$ alleles. Values represent averages of at least two fruits each from a minimum of four plants. Standard errors are in parentheses.

| | mg.g$^{-1}$ of fresh weight (s.e.) | | | | |
|---|---|---|---|---|---|
| Allelic state at Solyc12g099190 | Sucrose | Glucose | Fructose | Total soluble sugars | % sucrose (of total sugars) |
| SucMod$^{chm/chm}$ | 15.8 | 8.1 | 10.1 | 34.0 | 46.2 |
| | (1.2) | (0.6) | (0.6) | (2.2) | (1.7) |
| SucMod$^{chm}$/VIF$^{lyc}$ | 16.0 | 8.1 | 11.0 | 35.1 | 45.1 |
| | (0.8) | (0.4) | (0.4) | (1.5) | (0.9) |
| VIF$^{lyc/lyc}$ | 4.9 | 10.0 | 13.8 | 28.7 | 16.4 |
| | (0.8) | (0.7) | (0.8) | (1.9) | (1.9) |

Figure 3A:
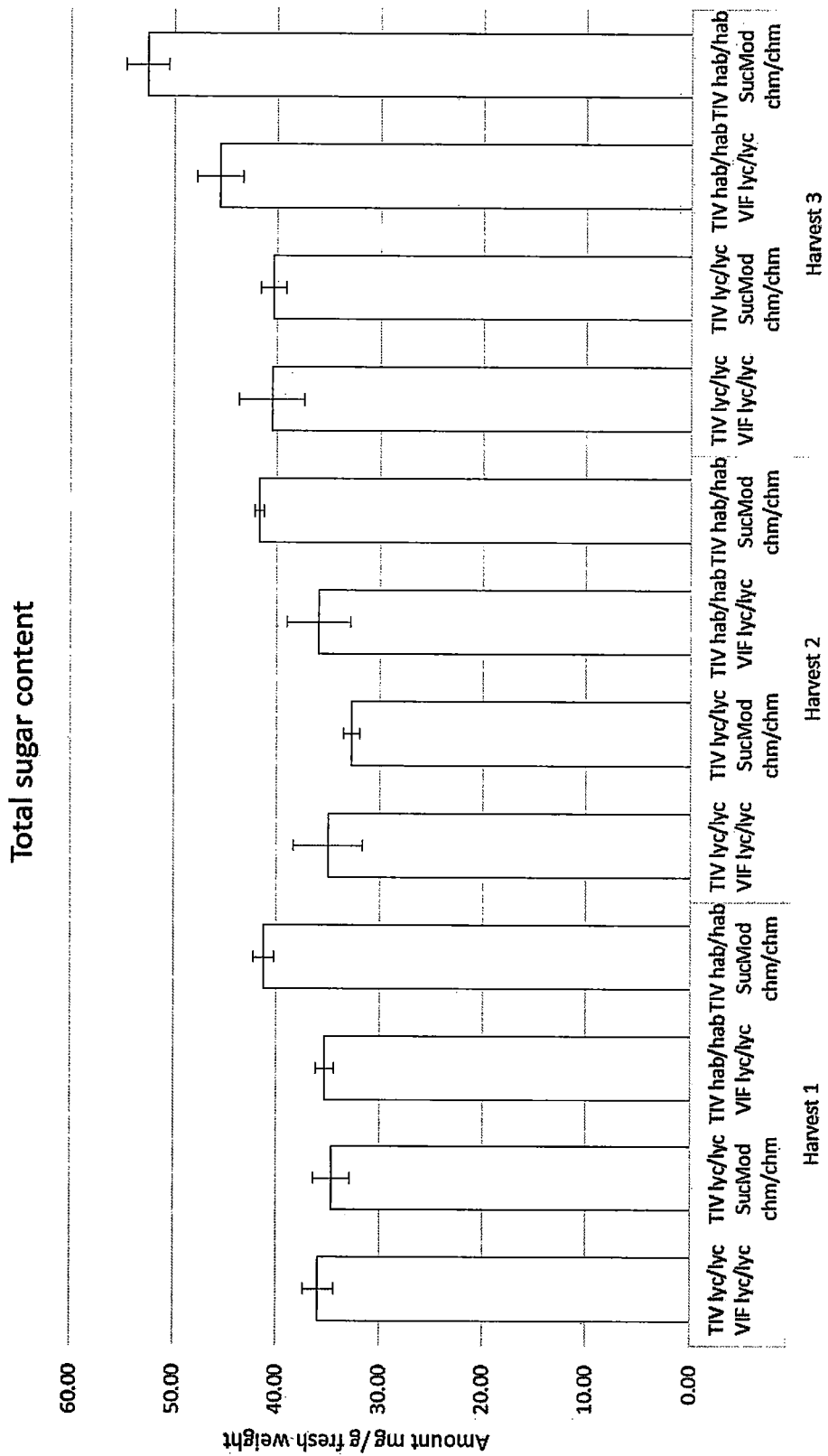
FIG. 3A shows Total sugar content
Figure 3B:
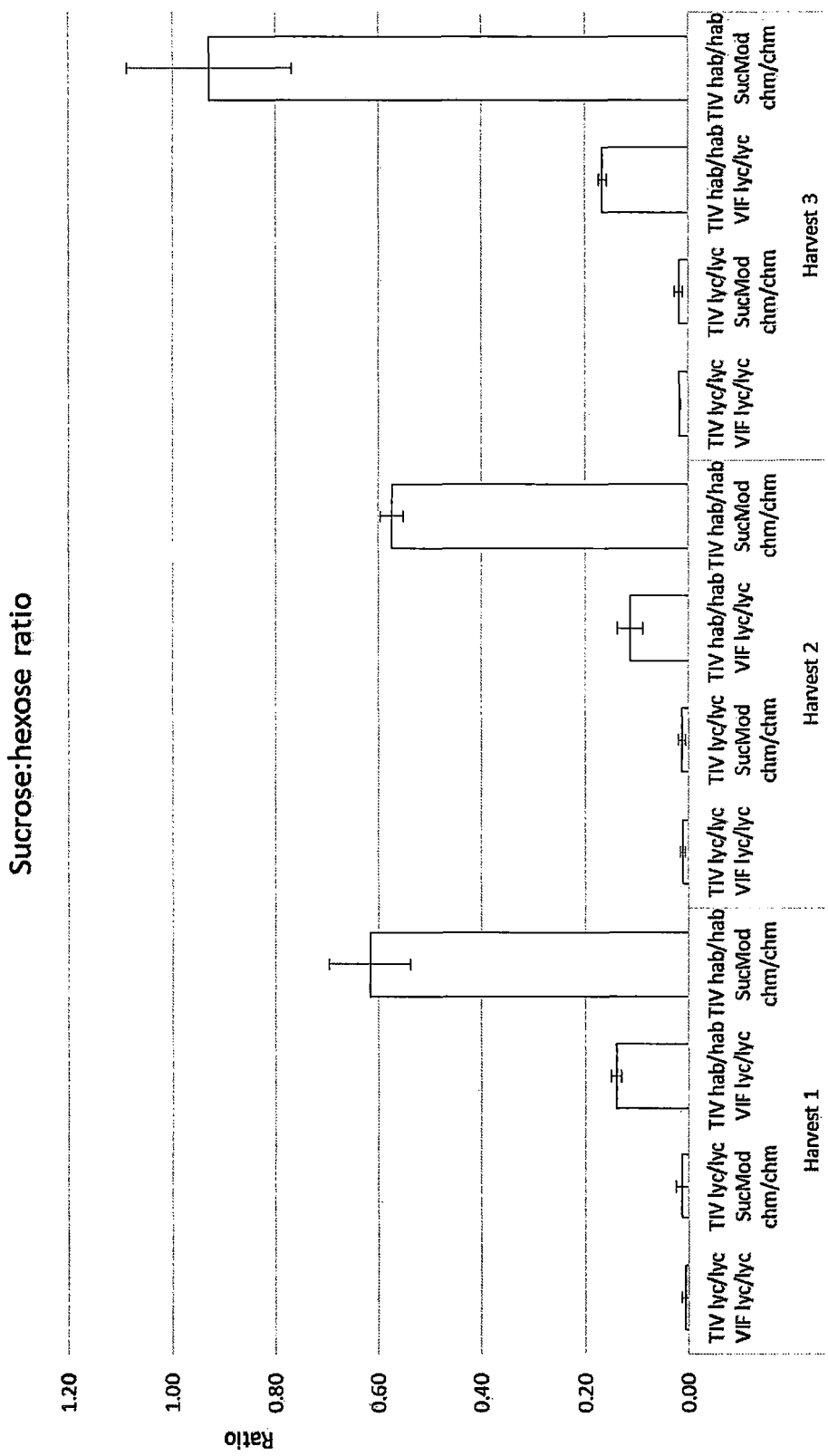
—FIG. 3B shows Sucrose to hexose ratio, in red ripe fruit of SucMod$^{chm/chm}$ and VIF$^{lyc/lyc}$ tomato lines in the TIV$^{lyc/lyc}$ or TIV$^{hab/hab}$ background. Plants were grown in passive protected conditions in randomised plots comprising six plants per plot.

Example 4: Confirmation of the Effect of the SucMod/VIF Alleles on Sucrose and Sugar Contents in a Different Genetic Background and a Different Location In order to confirm the effect of the SucMod/VIF alleles, sugar levels were measured on F6 tomato lines derived from tomato (*Solanum lycopersicum*) Ikram parental lines, segregating for the TIV$^{lyc/lyc}$, TIV$^{hab/hab}$, VIF$^{lyc/lyc}$ and SucMod$^{chm/chm}$ alleles. The results are presented in Table 4 and FIG. 3, and demonstrate that sucrose accumulation and sucrose to hexose ratio is significantly higher when the SucMod$^{chm/chm}$ genotype is combined with the TIV$^{hab/hab}$ genotype.

TABLE 4

Sucrose accumulation in red ripe fruit of SucMod$^{chm/chm}$ and VIF$^{lyc/lyc}$ tomato lines in the TIV$^{lyc/lyc}$ or TIV$^{hab/hab}$ background (in mg.g$^{-1}$ of fresh weight). Plants were grown in passive protected conditions in randomised plots comprising six plants per plot. Approximately ten fruits per plot were pooled into a single homogenate to assess metabolite levels. Averages were taken from three plots +/− standard error. Repeat measurements were taken at three separate time points (harvest 1-3).

| | Sucrose content (mg.g$^{-1}$ of fresh weight) | | |
|---|---|---|---|
| Genotype | Harvest 1 | Harvest 2 | Harvest 3 |
| TIV$^{lyc/lyc}$ VIF$^{lyc/lyc}$ | 0.24 +/− 0.24 | 0.39 +/− 0.17 | 0.66 +/− 0.09 |
| TIV$^{lyc/lyc}$ SucMod$^{chm/chm}$ | 0.43 +/− 0.43 | 0.42 +/− 0.22 | 0.73 +/− 0.27 |
| TIV$^{hab/hab}$ VIF$^{lyc/lyc}$ | 4.24 +/− 0.13 ** | 3.71 +/− 0.97 * | 6.44 +/− 0.05 ** |
| TIV$^{hab/hab}$ SucMod$^{chm/chm}$ | 15.42 +/− 1.34 ** | 15.20 +/− 0.43 ** | 25.17 +/− 3.27 ** |

Significance using Student's t-test: * <0.05; ** <0.01.

Example 5: Sequence Information for VIF and TIV Alleles, Including Exemplary Associated Snp Markers Table 5 recites the nucleotide sequence of the SucMod$^{chm}$ allele (SEQ ID NO: 1) and the TIV$^{hab}$ allele (SEQ ID NO: 6) of the invention. Furthermore, Table 5 discloses exemplary SNP molecular markers which are specifically associated with the SucMod$^{chm}$ allele (marker ST3226) and the TIV$^{hab}$ allele (markers ST3472 and ST3478). For each marker, the table shows the chromosome location, the primers (forward and reverse) to amplify the marker DNA fragment and favourable/recurrent probes identifying the targeted genotype. The favourable SNP allele is underlined and shown in bold in both the allele sequence and the favourable probe, and its position in reference to the allelic sequence is indicated.

TABLE 5

Nucleotide sequences of SEQ ID NO. 1-14.

| Chromosome/ Marker name | Sequence type | Nucleotide sequence | Detected nucleotide | SEQ ID |
|---|---|---|---|---|
| 12 | SucMod$^{chm}$ allele. Coding Sequence. | ATGAGAAATTTATTCCC CATATTGATGTTAATCAC TAATTTGGCACTCAACA ACGATAACAACAACAAC AACAACATCATACACGC AACGTGTAGGGAGACTC CATACTACTCCCTATGT CTCTCAGTCCTAGAATC CGATCCACGTAGCTACA AGGCTGAGGGTAGTGAT GATATAACCACCCTAGG TCTCATCATGGTGGATG CAGTGAAATCAAAGTCT ATAGAAATAATGAAAAA GCTAAAAGAGCTAGAGA AATCGAACCCTGAGTGG CGGGTCCCACTTAACCA GTGTTACATGGTGTATA ACGCCGTCCTACGAGC CGATGTAACGGTAGCCG TTGAAGCCTTGAAGAGG GGTGTCCCTAAATTTGC TGAAGATGGTATGGATG ATGTTGTTGTAGAAGCA CAAACTTGTGAGTTTAG TTTTAATTATTATAATAA ATCGGATTTTCCAATTTC TAATATGAGTAAGGACA TAGTTGAACTCTCAAAA GTTGCTAAATCCATAATT AGAATGTTATTATG | N/A | SEQ ID NO. 1 |
| 12/ST3226F1 | Forward primer | GGGTCCCACTTAACCA | N/A | SEQ ID NO. 2 |
| 12/ST3226R1 | Reverse primer | CGGCTACCGTTACATC | N/A | SEQ ID NO. 3 |
| 12/ ST3226A1FM | Probe favourable allele (complementary sequence) | CGTAGGACGGCGTTAT | G Position 310 of SEQ ID NO: 1 | SEQ ID NO. 4 |
| 12/ ST3226A1TT | Probe recurrent *lycopersicum* allele (complementary sequence) | TCGTAGGACGGTGTTAT | A Position 310 of SEQ ID NO: 1 | SEQ ID NO. 5 |
| 3 | TIV$^{hab}$ allele. Coding Sequence | ATGGCCACCCAGTGTTA TGACCCCGAAAACTCCG CCTCTCATTACACATTC CTCCCGGATCAACCCGA TTCCGGCCACCGGAAGT CCCTTAAAATCTTCTCC GGCATTTTCCTCTCCGT TTTCCTTTTGCTTTCTGT AGCCTTYTTTCCGATCC TCAACAACCAGTCACCG GACTTGCGAATCGACTC CCGTTCGCCGGCGCCG CCGTCAAGAGGTGTTTC TCAGGGAGTCTCTGATA | | SEQ ID NO. 6 |

TABLE 5-continued

Nucleotide sequences of SEQ ID NO. 1-14.

| Chromosome/<br>Marker name | Sequence type | Nucleotide sequence | Detected<br>nucleotide | SEQ ID |
|---|---|---|---|---|
| | | AAACTTTTCGAGATGTA | | |
| | | GCCGGTGCTAGTCACGT | | |
| | | TTCTTATGCGTGGTCCA | | |
| | | ATGCTATGCTTAGCTGG | | |
| | | CAAAGAACGGCTTACCA | | |
| | | TTTTCAACCTCAGAAAAA | | |
| | | TTGGATGAACGATCCTA | | |
| | | ATGGACCATTGTATCAC | | |
| | | AAGGGATGGTACCACCT | | |
| | | TTTTTATCAATACAATCC | | |
| | | AGATTCGGCTATTTGGG | | |
| | | GGAATATCACATGGGGC | | |
| | | CATGCTGTATCCAAGGA | | |
| | | CTTGATCCACTGGCTCT | | |
| | | ACTTGCCTTTTGCCATG | | |
| | | GTTCCTGATCAGTGGTA | | |
| | | TGATATTAACGGTGTCT | | |
| | | GGACAGGGTCCGCTAC | | |
| | | CATCCTACCCGATGGTC | | |
| | | AGATCATGATGCTTTATA | | |
| | | CCGGTGACACGGATGAT | | |
| | | TATGTACAAGTGCAAAA | | |
| | | TCTTGCGTACCCCGCCA | | |
| | | ACTTATCTGATCCTCTC | | |
| | | CTTCTAGACTGGGTCAA | | |
| | | GTACAAAGGCAACCCG | | |
| | | GTTCTGGTTCCTCCACC | | |
| | | CGGCATTGGGGTCAAG | | |
| | | GACTTTAGAGACCCGAC | | |
| | | TACTGCTTGGACCGGAC | | |
| | | CGCAAAATGGGCAATGG | | |
| | | CTGTTAACAATCGGGTC | | |
| | | CAAGATTGGTAAAACGG | | |
| | | GTATTGCACTTGTTTATG | | |
| | | AAACTTCCAACTTCACA | | |
| | | AGCTTTAAGCTATTGGA | | |
| | | TGGAGTGCTGCATGCG | | |
| | | GTTCCGGGTACGGGTAT | | |
| | | GTGGGAGTGTGTGGAC | | |
| | | TTTTACCCGGTGTCTAC | | |
| | | TAAAAAAACAAATGGGT | | |
| | | TGGACACATCATATAAC | | |
| | | GGGCCGGGTGTAAAGC | | |
| | | ATGTGTTAAAAGCAAGT | | |
| | | TTAGATGACAATAAGCA | | |
| | | AGATCATTATGCTATTG | | |
| | | GTACGTATGACTTGACA | | |
| | | AAGAACAAATGGACACC | | |
| | | CGAC<u>C</u>AACCCGGAATTKG | | |
| | | ATT<u>G</u>TGGAATTGGGTTG | | |
| | | AGACTAGACTATGGGAA | | |
| | | ATATTATGCATCAAAGA | | |
| | | CTTTTTATGACCCGAAG | | |
| | | AAACAACGAAGAGTACT | | |
| | | GTGGGGATGGATTGGG | | |
| | | GAAACTGACAGTGAATC | | |
| | | TGCTGACCTGCAGAAGG | | |
| | | GATGGGCATCTGTACAG | | |
| | | AGTATTCCAAGGACAGT | | |
| | | GCTTTACGACAAGAAGA | | |
| | | CAGGGACACATCTACTT | | |
| | | CAGTGGCCAGTGGAAG | | |
| | | AAATTGAAAGCTTAAGA | | |
| | | GTGGGTGATCCTATTGT | | |
| | | TAAGCAAGTCGATCTTC | | |
| | | AACCAGGCTCAATTGAG | | |
| | | CTACTCCGTGTTGACTC | | |
| | | AGCTGCAGAGTTGGATA | | |
| | | TAGAAGTCTCATTTGAA | | |
| | | GTGGACAAAGTCGCGCT | | |
| | | TCAGGGAATAATTGAAG | | |
| | | CAGATCATGTTGGTTTC | | |
| | | AGTTGCTCTACTAGTGG | | |
| | | AGGTGCTGCTAGCAGA | | |
| | | GGCATTTTGGGACCGTT | | |

TABLE 5-continued

Nucleotide sequences of SEQ ID NO. 1-14.

| Chromosome/ Marker name | Sequence type | Nucleotide sequence | Detected nucleotide | SEQ ID |
|---|---|---|---|---|
| | | TGGTGTCATAGTGATTG CTGATCAAACGCTATCT GAGCTAACGCCAGTTTA CTTCTACATTTCTAAAGG AGCTGATGGTCGTGCAG AGACTCACTTCTGTGCT GATCAAACTAGATCCTC AGAGGCTCCGGGAGTT GGTAAACAAGTTTATGG TAGTTCAGTACCTGTGT TGGACGGTGAAAAACAT TCAATGAGATTATTGGT GGATCACTCAATTGTGG AGAGCTTTGCTCAAGGA GGAAGAACAGTCATAGC ATCGCGAATTTACCCAA CAAAGGCAGCAAATGGA GCAGCACGACTCTTCGT TTTCAACAATGCTACAG GGGCTAGCGTTACTGCC TCCGTCAAGATTTGGTC ACTTGACTCAGCTAATA TTCGATCCCTCCCTTTG CAAGACTTGTAA | | |
| 3/ST3472F1 | Forward primer | AGTCTCAACCCAATTCC ACAATCC | N/A | SEQ ID NO. 7 |
| 3/ST3472R1 | Reverse primer | GGTTCCGGGTACGGGT ATG | N/A | SEQ ID NO. 8 |
| 3/ ST3472A1TT | Probe favourable allele (complementary sequence) | AATTCCGGGTTGTCG | C Position 1056 of SEQ ID NO: 6 | SEQ ID NO. 9 |
| 3/ ST3472A1FM | Probe recurrent allele (complementary sequence) | AATTCCGGGTTATCGG | T Position 1056 of SEQ ID NO: 6 | SEQ ID NO. 10 |
| 3/ST3478F1 | Forward primer | TGCTTTCTGTAGCCTTC TTTCC | N/A | SEQ ID NO. 11 |
| 3/ST3478R1 | Reverse primer | TGCCAGCTAAGCATAGC ATTG | N/A | SEQ ID NO. 12 |
| 3/ ST3478A1TT | Probe favourable allele (sense sequence) | CGGACTTGCGAATCGA | G Position 179 of SEQ ID NO: 6 | SEQ ID NO. 13 |
| 3/ ST3478A1FM | Probe recurrent allele (sense sequence) | CGGACTTGCAAATCGA | A Position 179 of SEQ ID NO: 6 | SEQ ID NO. 14 |

Example 6: Identification of Additional SucMod/VIF Alleles in Other Wild Tomato Species In order to identify potential new genetic sources for orthologous SucMod/VIF alleles, soluble sugar levels of mature fruits of wild and cultivated tomato species were measured. The results are disclosed in Table 6 and highlight that *Solanum* accessions from *habrochaites, pennellii, peruvianum* and *chmielewskii* are forming a subgroup for which the sucrose content is higher than 10 mg.g$^{-1}$ of fresh weight, and the sucrose to hexose ratio is about or greater than 2. On the other hand, the *Solanum* accessions *lycopersicum, cheesmaniae* and *pimpinellifolium* are forming another subgroup for which the sucrose content is about or less 3 mg.g$^{-1}$ of fresh weight, and the sucrose to hexose ratio is below 0.2. The nature of the former subgroup is further confirmed by the expression data of their corresponding TIV and VIF alleles from the *habrochaites, pennellii, peruvianum* and *chmielewskii* accessions. All accessions in the subgroup show a high level of expression of the VIF allele and a low level of expression of the TIV allele. On the contrary, at least the *lycopersicum* and *cheesmaniae* accessions exhibit a reverse expression profile: the TIV allele is highly expressed and the VIF allele is hardly expressed. From an expression level standpoint, the *pimpinellifolium* accessions seem to form a separate third subgroup whereby the TIV allele is highly expressed, as is the VIF allele.

These data indicate that at least the *habrochaites*, pennelh pennelhi, *peruvianum* and *chmielewskii* but also the *pimpinellifolium* accessions can be used as genetic sources for additional SucMod/VIF alleles as long as they are used in combination with TIV alleles from green-fruited wild tomato accession to increase sucrose content, total sugar content and sucrose to hexose ratio.

TABLE 6

Sugar content of wild and cultivated tomato accessions.

| Solanum species | Accession | suc. | gluc. | fruct. | total | suc/hex. | RPKM TIV | RPKM VIF |
|---|---|---|---|---|---|---|---|---|
| lycopersicum | BD5337 | 0.8 | 10.3 | 11.2 | 22.2 | 0.0 | 368 | 3 |
| lycopersicum | BD5338 | 1.6 | 28.5 | 28.9 | 59.1 | 0.0 | 1211 | 3 |
| lycopersicum | BD7039 | 0.6 | 14.5 | 18 | 33.1 | 0.0 | 4521 | 4 |
| lycopersicum | MP-1 | 0.8 | 13.1 | 16.3 | 30.2 | 0.0 | 6795 | 19 |
| cheesmaniae | LA1036 | 0.7 | 1.3 | 5 | 6.9 | 0.1 | 432 | 17 |
| cheesmaniae | LA1412 | 3.1 | 2.5 | 14.2 | 19.9 | 0.2 | 106 | 26 |
| pimpinellifolium | LA1586 | 4.2 | 5.9 | 11.8 | 19.8 | 0.2 | 4025 | 1022 |
| pimpinellifolium | LA1589 | 1.3 | 8.5 | 15.1 | 24.9 | 0.1 | 2713 | 571 |
| habrochaites | LA1777 | 13.6 | 1.7 | 4 | 19.4 | 2.4 | 6 | 613 |
| habrochaites | LA0407 | 25.8 | 3.7 | 8.5 | 38.1 | 2.1 | 17 | 744 |
| pennellii | LA0716 | 25.2 | 5.7 | 6.7 | 37.6 | 2.0 | 11 | 644 |
| peruvianum | PI126431 | 24 | 1.5 | 10.9 | 36.4 | 1.9 | 5 | 823 |
| peruvianum | PI126926 | 39.8 | 1.8 | 4.3 | 45.8 | 6.5 | 16 | 428 |
| chmielewskii | LA1028 | 32.8 | 2.1 | 4.1 | 39 | 5.2 | 3 | 983 |
| chmielewskit | LA13.18 | 20.1 | 1.1 | 3.2 | 24.5 | 4.7 | 77 | 1055 |
| chmielewskii | BD732 | 35.9 | 2 | 3.5 | 41.4 | 6.6 | 2 | 1375 |

Sugar data are expressed in mg · g$^{-1}$ of fresh weight.
Expression data of the TIV (corresponding to Solyc03g083910) and VIF (corresponding to Solyc12g099190) alleles are expressed in RPKM values derived from RNAseq data.
Accession numbers are from TGRC (LA), USDA-ARS (PI) or from ARO research breeding lines (BD).
At least three red ripe fruits for each accession were analysed.

To further investigate whether additional SucMod/VIF alleles can be sourced in other wild tomato species, sequence alignments using Clustal Omega were carried out using the SucMod/VIF allelic sequences of *Solanum lycopersicum*, *Solanum chmielewskii* BD732 and *Solanum pennellii* LA0716, and the homologous sequences from *Solanum cheesmaniae* LA0429, and *Solanum pimpinellifolium* LA1589.

FIG. 4 shows that the VIF allele of *Solanum pimpinellifolium* LA1589 (VIF$^{pimp}$) exhibits the same polymorphism at SNP marker ST3226 than what was identified for the SucMod$^{chm}$ allele, namely a nucleotide G at a position which corresponds to position 310 of SEQ ID NO: 1 (see also Table 5). The SucMod$^{chm}$ allele and the VIF$^{pimp}$ allele additionally share another SNP, namely a nucleotide T at a position which corresponds to position 498 of SEQ ID NO: 1.

Finally, the VIF$^{pimp}$ allele and the SucMod$^{chm}$ allele share 98.86% genetic identity over their whole sequences.

It is therefore expected that at least the VIF$^{pimp}$ *Solanum pimpinellifolium* allele from accession LA1589 provides similar effects to those observed with the SucMod$^{chm}$ allele on sucrose accumulation, total sugar content and sucrose to hexose ratio.

Example 7: Identification of Additional TIV Alleles in Other Wild Tomato Species The results disclosed in Table 6 and discussed in Example 7 also suggest that green-fruited *Solanum* accessions from *habrochaites, pennellii, peruvianum* and *chmielewskii* could also be used as genetic sources for additional TIV alleles to work in combination with the SucMod/VIF alleles of the invention towards an increased sucrose content.

To further investigate whether additional TIV alleles can indeed be sourced in other wild tomato species, sequence alignments using Clustal Omega were carried out using the TIV allelic sequences of *Solanum habrochaites* (SEQ ID NO: 6), *Solanum peruvianum, Solanum pennellii, Solanum chmielewskii, Solanum lycopersicum, Solanum lycopersicum* var *cerasiforme, Solanum cheesmaniae* and *Solanum pimpinellifolium* and are shown in FIG. 5.

FIG. 5 shows that the TIV alleles of *Solanum habrochaites* (SEQ ID NO: 6), *Solanum peruvianum, Solanum pennellii* and *Solanum chmielewskii* exhibit identical polymorphisms at 8 positions, which are highlighted in bold and with a grey shade, thereby providing 8 SNP markers for discriminating the TIV alleles of the *habrochaites/peruvianum/pennellii/chmielewskii* subgroup. Two different SNP markers exhibit a polymorphism specific for the sole *Solanum habrochaites* TIV$^{hab}$ allele from accession LA1777 and are also highlighted in bold and with a grey shade. The latter SNP markers, ST3472 and ST3478 for which additional relevant sequence information can be found in Table 5, have been effectively used to discriminate the TIV$^{hab}$ allele.

Furthermore, the TIV alleles of green-fruited *Solanum habrochaites* (SEQ ID NO: 6), *Solanum peruvianum, Solanum pennellii* and *Solanum chmielewskii* share at least 98% genetic identity over their whole sequences.

Example 8: Exemplary Protocol to Analyse Sugar Content of Tomato Fruits

Samples of pericarp tissues of the tomato fruits (ca 1 g fresh weight FW) were extracted 3 times in 5 ml of 80% (v:v) ethanol for 45 min at 70° C., the three extracts were pooled. The sugar solution was then evaporated to dryness at 75° C. and redissolved in 2 ml distilled water. Analysis of soluble sugars was performed by high performance liquid chromatography (HPLC, Shimadzu, Japan) using an Alltech 700CH Carbohydrate column (Alltech Associates, catalog number 70057) and refractive index detector (RID-10A, Shimadzu, Japan), as previously described in Miron and Schaffer 1991.

Alternatively, analysis of sucrose and hexose sugars can be done using available UV methodologies, such as ENZYTEC D-Glucose/D-Fructose/Sucrose available from R-Biopharm AG. Sugar concentrations are quantified based on changes in UV absorbance readings over time of sugar solutions in the presence of commercially available enzyme kits containing β-fructosidase, hexokinase, phosphoglucose isomerase, and glucose-6-phosphate dehydrogenase."

BIBLIOGRAPHY

Davies J. N., 1966, Occurrence of sucrose in the fruit of some species of *Lycopersicon, Nature* 209, p. 640-641.
Manning K. and Maw G. A., 1975, Distribution of acid invertase in the tomato plant, Phytochemistry 14(9), p. 1965-1969.
Yelle S. et al., 1991, Sink metabolism in tomato fruit: IV. Genetic and biochemical analysis of sucrose accumulation, Plant Physiol. 95(4), p. 1026-1035.
Stommel J. R., 1992, Enzymic Components of Sucrose Accumulation in the Wild Tomato Species *Lycopersicon peruvianum*, Plant Physiol. 99(1), p. 324-328.
Klann E. et al., 1993, Expression of acid invertase gene controls sugar composition in tomato (*lycopersicon*) fruit, Plant Physiol. 103(3), p. 863-870.
Chetelat R. T. et al., 1993, Inheritance and genetic mapping of fruit sucrose accumulation in *Lycopersicon chmielewskii*, Plant J. 4, p. 643-650.
Hadas R. et al., 1995, PCR-generated molecular markers for the invertase gene and sucrose accumulation in tomato, Theor. Appl. Genet. 90(7-8), p. 1142-1148.
Miron D. et al., 2002, Sucrose uptake, invertase localization and gene expression in developing fruit of *Lycopersicon esculentum* and the sucrose-accumulating *Lycopersicon hirsutum*, Physiol. Plant. 115(1), p. 35-47.
Jin Y. et al., 2009, Posttranslational elevation of cell wall invertase activity by silencing its inhibitor in tomato delays leaf senescence and increases seed weight and fruit hexose level, Plant Cell 21, p. 2072-2089.
Sievers F. et al., 2011, Fast, scalable generation of high-quality protein multiple sequence alignments using Clustal Omega, Mol. Syst. Biol. 7:539.
Tauzin A. S. et al., 2014, Functional characterization of a vacuolar invertase from *Solanum lycopersicon*: posttranslational regulation by N-glycosylation and a proteinaceous inhibitor, Biochimie 101, p. 39-49.
Qin G. et al., 2016, A tomato vacuolar invertase inhibitor mediates sucrose metabolism and influences fruit ripening, Plant Physiol. 172, p. 1596-1611.
Miron D. and Schaffer A. A., 1991, Sucrose Phosphate Synthase, Sucrose Synthase, and Invertase Activities in Developing Fruit of *Lycopersicon esculentum* Mill. and the Sucrose Accumulating *Lycopersicon hirsutum* Humb. and Bonpl., Plant Physiol. 95(2), p. 623-627.

The invention claimed is:

1. A cultivated *Solanum lycopersicum* plant, comprising:
   a) at least one Sucrose Modifier (SucMod) allele having at least 97% sequence identity with SEQ ID NO: 1, and
   b) two sucrose accumulation Tomato Vacuolar Invertase (TIV) alleles having at least 98% sequence identity with SEQ ID NO: 6;
wherein said SucMod allele comprises a nucleotide G at a position which corresponds to position 310 of SEQ ID NO: 1, and a nucleotide T at a position which corresponds to position 498 of SEQ ID NO: 1,
wherein said TIV allele and said SucMod allele are comprised in *Solanum lycopersicum* line TIPC18-61141, deposited with NCIMB on 20 Aug. 2018 under NCIMB Accession No. 43169, and
wherein said plant produces tomato fruit exhibiting an increased sucrose content compared with the same cultivated tomato plant lacking said SucMod and TIV alleles.

2. The plant of claim 1, wherein said SucMod allele is obtained from *Solanum chmielewskii* or *Solanum pimpinellifolium*.

3. The plant of claim 1, wherein said SucMod allele comprises the nucleotide sequence of SEQ ID NO: 1.

4. The plant of claim 1, wherein said TIV allele comprises a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

5. The plant of claim 1, wherein said TIV allele is obtained from *Solanum habrochaites*.

6. The plant of claim 4, wherein said TIV allele further comprises a nucleotide C at a position which corresponds to position 1056 of SEQ ID NO: 6; and/or a nucleotide G at a position which corresponds to position 179 of SEQ ID NO: 6.

7. The plant of claim 1, wherein said TIV allele comprises the nucleotide sequence of SEQ ID NO: 6.

8. The plant of claim 1, wherein said plant comprises two copies of the SucMod allele.

9. A seed that produces the plant of claim 1.

10. A method of producing a cultivated *Solanum lycopersicum* plant producing tomato fruits exhibiting increased sucrose content comprising the steps of:
   a) crossing the plant according to claim 1 comprising at least one sucrose modifier SucMod allele and two sucrose accumulation TIV alleles with a cultivated tomato plant lacking said SucMod and TIV alleles; and
   b) selecting a progeny plant producing fruits exhibiting an increased sucrose content compared with the same cultivated tomato plant lacking said SucMod and TIV alleles;
wherein the selecting in step b) is carried out by detecting a nucleotide G at a position which corresponds to position 310 of SEQ ID NO: 1, and/or a nucleotide T at a position which corresponds to position 498 of SEQ ID NO: 1; and, by detecting a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6; and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6.

11. The method of claim 10 wherein the selecting in step b) is carried out by further detecting a nucleotide C at a position which corresponds to position 1056 of SEQ ID NO: 6; and/or a nucleotide G at a position which corresponds to position 179 of SEQ ID NO: 6.

12. A method of identifying the cultivated *Solanum lycopersicum* plant according to claim 1, comprising the steps of:
   a) detecting in said cultivated *Solanum lycopersicum* plant a nucleotide G at a position which corresponds to position 310 of SEQ ID NO: 1, and/or a nucleotide T at a position which corresponds to position 498 of SEQ ID NO: 1;
   b) detecting in said cultivated *Solanum lycopersicum* plant a nucleotide A at a position which corresponds to position 41 of SEQ ID NO: 6; and/or a nucleotide A at a position which corresponds to position 668 of SEQ ID NO: 6; and/or a nucleotide T at a position which corresponds to position 930 of SEQ ID NO: 6;
   and/or a nucleotide C at a position which corresponds to position 1034 of SEQ ID NO: 6; and/or a nucleotide T at a position which corresponds to position 1319 of SEQ ID NO: 6; and/or a nucleotide C at a position which corresponds to position 1563 of SEQ ID NO: 6; and/or a nucleotide A at a position which corresponds to position 1629 of SEQ ID NO: 6; and/or a nucleotide G at a position which corresponds to position 1886 of SEQ ID NO: 6; and, c) identifying, based on the detecting, a cultivated *Solanum lycopersicum* plant producing fruits exhibiting an increased sucrose content compared with the same cultivated tomato plant lacking said SucMod and TIV alleles.

13. The method of claim 12 wherein step b) is carried out by further detecting a nucleotide C at a position which corresponds to position 1056 of SEQ ID NO: 6; and/or a nucleotide G at a position which corresponds to position 179 of SEQ ID NO: 6.

14. A cultivated *Solanum lycopersicum* plant, comprising:
a) at least one Sucrose Modifier (SucMod) allele comprising the nucleotide sequence of SEQ ID NO: 1, and
b) two sucrose accumulation Tomato Vacuolar Invertase (TIV) alleles, each comprising the nucleotide sequence of SEQ ID NO: 6;

wherein said plant produces tomato fruit exhibiting an increased sucrose content compared with the same cultivated tomato plant lacking said SucMod and TIV alleles.

15. The plant of claim 14, wherein said plant comprises two copies of the SucMod allele.

16. A seed that produces the plant of claim 14.

17. A method of producing a cultivated *Solanum lycopersicum* plant producing tomato fruits exhibiting increased sucrose content comprising:
a) crossing the plant according to claim 14 with a cultivated tomato plant lacking said SucMod and TIV alleles; and
b) selecting a progeny plant producing fruits exhibiting an increased sucrose content compared with the same cultivated tomato plant lacking said SucMod and TIV alleles;

wherein the selecting in step b) is carried out by detecting a nucleotide G at position 310 of SEQ ID NO: 1, and/or a nucleotide T at position 498 of SEQ ID NO: 1; and, by detecting a nucleotide A at position 41 of SEQ ID NO: 6; and/or a nucleotide A at position 668 of SEQ ID NO: 6; and/or a nucleotide T at position 930 of SEQ ID NO: 6; and/or a nucleotide C at position 1034 of SEQ ID NO: 6; and/or a nucleotide T at position 1319 of SEQ ID NO: 6; and/or a nucleotide C at position 1563 of SEQ ID NO: 6; and/or a nucleotide A at position 1629 of SEQ ID NO: 6; and/or a nucleotide G at position 1886 of SEQ ID NO: 6.

18. A method of identifying the plant of claim 14, comprising:
a) detecting a nucleotide G at position 310 of SEQ ID NO: 1, and a nucleotide T at position 498 of SEQ ID NO: 1;
b) detecting a nucleotide A at position 41 of SEQ ID NO: 6; a nucleotide A at position 668 of SEQ ID NO: 6; a nucleotide T at position 930 of SEQ ID NO: 6; a nucleotide C at position 1034 of SEQ ID NO: 6; a nucleotide T at position 1319 of SEQ ID NO: 6; a nucleotide C at position 1563 of SEQ ID NO: 6; a nucleotide A at position 1629 of SEQ ID NO: 6; and a nucleotide G at position 1886 of SEQ ID NO: 6; and
c) identifying, based on the detecting, a cultivated *Solanum lycopersicum* plant producing fruits exhibiting an increased sucrose content compared with the same cultivated tomato plant lacking said SucMod and TIV alleles.

19. The method of claim 18, wherein step b) is carried out by further detecting a nucleotide C at position 1056 of SEQ ID NO: 6; and/or a nucleotide G at position 179 of SEQ ID NO: 6.

* * * * *